(12) United States Patent
Xie et al.

(10) Patent No.: US 9,617,598 B2
(45) Date of Patent: Apr. 11, 2017

(54) METHODS OF AMPLIFYING WHOLE GENOME OF A SINGLE CELL

(75) Inventors: Xiaoliang Sunney Xie, Lexington, MA (US); Chenghang Zong, Houston, TX (US); Sijia Lu, Beijing (CN)

(73) Assignee: President and Fellows of Harvard College, Cambridge, MA (US)

( * ) Notice: Subject to any disclaimer, the term of this patent is extended or adjusted under 35 U.S.C. 154(b) by 481 days.

(21) Appl. No.: 14/122,341

(22) PCT Filed: May 22, 2012

(86) PCT No.: PCT/US2012/038930
§ 371 (c)(1),
(2), (4) Date: Mar. 19, 2014

(87) PCT Pub. No.: WO2012/166425
PCT Pub. Date: Dec. 6, 2012

(65) Prior Publication Data
US 2014/0200146 A1    Jul. 17, 2014

Related U.S. Application Data

(60) Provisional application No. 61/490,790, filed on May 27, 2011, provisional application No. 61/550,677, filed on Oct. 24, 2011, provisional application No. 61/510,539, filed on Jul. 22, 2011, provisional application No. 61/621,271, filed on Apr. 6, 2012.

(51) Int. Cl.
*C12Q 1/68* (2006.01)
*C12P 19/34* (2006.01)
*C12N 15/10* (2006.01)

(52) U.S. Cl.
CPC ....... *C12Q 1/6883* (2013.01); *C12N 15/1093* (2013.01); *C12Q 1/6848* (2013.01); *C12Q 1/6886* (2013.01)

(58) Field of Classification Search
None
See application file for complete search history.

(56) References Cited

U.S. PATENT DOCUMENTS

| | | |
|---|---|---|
| 2003/0100006 A1 | 5/2003 | Senapathy |
| 2003/0108870 A1 | 6/2003 | Ji et al. |
| 2004/0126764 A1 | 7/2004 | Lasken et al. |
| 2004/0209298 A1 | 10/2004 | Kamberov et al. |
| 2005/0019793 A1 | 1/2005 | Kurn et al. |
| 2005/0202490 A1 | 9/2005 | Makarov et al. |
| 2009/0018031 A1 | 1/2009 | Trinklein et al. |
| 2009/0291475 A1 | 11/2009 | Lao et al. |

FOREIGN PATENT DOCUMENTS

WO    2004081225 A2    9/2004

OTHER PUBLICATIONS

Office Action issued for corresponding Chinese Patent Application No. 201280037511.X, dated Nov. 30, 2015.
Office Action issued for corresponding European Patent Application No. 12793376.0, dated Jan. 22, 2016.
Supplementary European Search Report issued from corresponding EP 12793376, dated Apr. 17, 2015.
Zong, Chenghang et al, "Genome-Wide Detection of Single-Nucleotide and Copy-Number Variations of a Single Human Cell,"Science.vol. 338. No. 6114. Dec. 20, 2012 (Dec. 20, 2012). pp. 1622-1626. XP055183862. ISSN: 0036-8075. DOI: 10.1126jscience.1229164 the whole document.
International Search Report from corresponding PCT/US2012/038930, dated Nov. 23, 2012.
International Preliminary Report on Patentability from corresponding PCT/US2012/038930, dated Apr. 3, 2014.
Goetz et al., "Oncorhynchus mykiss regulator of G-protein signalling 14 mRNA, complete cds" GenBank Accession No. AY606041, May 1, 2006, 2 pages (retrieved from the internet on Nov. 1, 2012) <url:http://www.ncbi.nlm.nih.gov/nuccore/ay606041>.
Pelak et al., The characterization of twenty sequenced human genomes. PLoS Genetics, Sep. 9, 2010, pp. 1-10, vol. 6, No. 9, Article e1001111.
Regier et al., "Increased yield of PCR product from degenerate primers with nondegenerate, nonhomologous 5' tails" Biotechniques, Jan. 2005, pp. 34-38, vol. 38, No. 1.
Fan et al., "Whole-genome molecular haplotyping of single cells" Nature Biotechnology, Jan. 2011, pp. 51-57, vol. 29, No. 1.
Office Action issued in corresponding Chinese Application No. 201280037511.x, dated Jan. 7, 2015.

*Primary Examiner* — David Thomas
(74) *Attorney, Agent, or Firm* — Banner & Witcoff, Ltd.

(57) ABSTRACT

Methods and compositions for amplifying the whole genome of a single cell are provided.

11 Claims, 6 Drawing Sheets

SEQUENCE LISTING

```
<160> NUMBER OF SEQ ID NOS: 39

<210> SEQ ID NO 1
<211> LENGTH: 35
<212> TYPE: DNA
<213> ORGANISM: artificial
<220> FEATURE:
<223> OTHER INFORMATION: amplification primer
<220> FEATURE:
<221> NAME/KEY: misc_feature
<222> LOCATION: (28)..(32)
<223> OTHER INFORMATION: n is a, c, g, or t

<400> SEQUENCE: 1
gtgagtgatg gttgaggtag tgtggagnnn nnggg                              35

<210> SEQ ID NO 2
<211> LENGTH: 35
<212> TYPE: DNA
<213> ORGANISM: artificial
<220> FEATURE:
<223> OTHER INFORMATION: amplification primer
<220> FEATURE:
<221> NAME/KEY: misc_feature
<222> LOCATION: (28)..(32)
<223> OTHER INFORMATION: n is a, c, g, or t

<400> SEQUENCE: 2
gtgagtgatg gttgaggtag tgtggagnnn nnttt                              35

<210> SEQ ID NO 3
<211> LENGTH: 27
<212> TYPE: DNA
<213> ORGANISM: artificial
<220> FEATURE:
<223> OTHER INFORMATION: amplification primer

<400> SEQUENCE: 3
gtgagtgatg gttgaggtag tgtggag                                       27

<210> SEQ ID NO 4
<211> LENGTH: 28
<212> TYPE: DNA
<213> ORGANISM: artificial
<220> FEATURE:
<223> OTHER INFORMATION: amplification primer
<220> FEATURE:
<221> NAME/KEY: misc_feature
<222> LOCATION: (19)..(19)
<223> OTHER INFORMATION: methylated

<400> SEQUENCE: 4
gtgagtgatg gttgaggtmc ttgtggag                                      28

<210> SEQ ID NO 5
<211> LENGTH: 35
<212> TYPE: DNA
<213> ORGANISM: artificial
<220> FEATURE:
<223> OTHER INFORMATION: amplification primer
```

```
<220> FEATURE:
<221> NAME/KEY: misc_feature
<222> LOCATION: (28)..(32)
<223> OTHER INFORMATION: n is a, c, g, or t

<400> SEQUENCE: 5
gtgagtgatg gttgaggtag tgtggagnnn nnggg                              35

<210> SEQ ID NO 6
<211> LENGTH: 35
<212> TYPE: DNA
<213> ORGANISM: artificial
<220> FEATURE:
<223> OTHER INFORMATION: amplification primer
<220> FEATURE:
<221> NAME/KEY: misc_feature
<222> LOCATION: (28)..(32)
<223> OTHER INFORMATION: n is a, c, g, or t

<400> SEQUENCE: 6
gtgagtgatg gttgaggtag tgtggagnnn nnttt                              35

<210> SEQ ID NO 7
<211> LENGTH: 27
<212> TYPE: DNA
<213> ORGANISM: artificial
<220> FEATURE:
<223> OTHER INFORMATION: amplification primer
<220> FEATURE:
<221> NAME/KEY: misc_feature
<222> LOCATION: (1)..(1)
<223> OTHER INFORMATION: biotinylated

<400> SEQUENCE: 7
gtgagtgatg gttgaggtag tgtggag                                       27

<210> SEQ ID NO 8
<211> LENGTH: 24
<212> TYPE: DNA
<213> ORGANISM: artificial
<220> FEATURE:
<223> OTHER INFORMATION: amplification primer

<400> SEQUENCE: 8
aggaaaggca tactggaggg acat                                          24

<210> SEQ ID NO 9
<211> LENGTH: 24
<212> TYPE: DNA
<213> ORGANISM: artificial
<220> FEATURE:
<223> OTHER INFORMATION: amplification primer

<400> SEQUENCE: 9
ttagggatgg caccacactc ttga                                          24

<210> SEQ ID NO 10
<211> LENGTH: 24
<212> TYPE: DNA
<213> ORGANISM: artificial
<220> FEATURE:
<223> OTHER INFORMATION: amplification primer

<400> SEQUENCE: 10
tcccagagaa gcatcctcca tgtt                                          24

<210> SEQ ID NO 11
```

<211> LENGTH: 24
<212> TYPE: DNA
<213> ORGANISM: artificial
<220> FEATURE:
<223> OTHER INFORMATION: amplification primer

<400> SEQUENCE: 11
caccacactg cctcaaatgt tgct                                          24

<210> SEQ ID NO 12
<211> LENGTH: 24
<212> TYPE: DNA
<213> ORGANISM: artificial
<220> FEATURE:
<223> OTHER INFORMATION: amplification primer

<400> SEQUENCE: 12
tcaagttgcc agctgtggct gtat                                          24

<210> SEQ ID NO 13
<211> LENGTH: 24
<212> TYPE: DNA
<213> ORGANISM: artificial
<220> FEATURE:
<223> OTHER INFORMATION: amplification primer

<400> SEQUENCE: 13
agaagggcat ttcctgtcag tgga                                          24

<210> SEQ ID NO 14
<211> LENGTH: 24
<212> TYPE: DNA
<213> ORGANISM: artificial
<220> FEATURE:
<223> OTHER INFORMATION: amplification primer

<400> SEQUENCE: 14
atgggcaaat ccagaagagt ccag                                          24

<210> SEQ ID NO 15
<211> LENGTH: 26
<212> TYPE: DNA
<213> ORGANISM: artificial
<220> FEATURE:
<223> OTHER INFORMATION: amplification primer

<400> SEQUENCE: 15
ccattcactt ccttggaaag gtagcc                                        26

<210> SEQ ID NO 16
<211> LENGTH: 24
<212> TYPE: DNA
<213> ORGANISM: artificial
<220> FEATURE:
<223> OTHER INFORMATION: amplification primer

<400> SEQUENCE: 16
aatagcgtgc agttctgggt agca                                          24

<210> SEQ ID NO 17
<211> LENGTH: 24
<212> TYPE: DNA
<213> ORGANISM: artificial
<220> FEATURE:
<223> OTHER INFORMATION: amplification primer

<400> SEQUENCE: 17
ttcacatcct gggaggaaca gcat                                          24

<210> SEQ ID NO 18
<211> LENGTH: 24
<212> TYPE: DNA
<213> ORGANISM: artificial
<220> FEATURE:
<223> OTHER INFORMATION: amplification primer

<400> SEQUENCE: 18
tgaatgccag ggtgagacct ttga                                          24

<210> SEQ ID NO 19
<211> LENGTH: 24
<212> TYPE: DNA
<213> ORGANISM: artificial
<220> FEATURE:
<223> OTHER INFORMATION: amplification primer

<400> SEQUENCE: 19
tgttcattat cccacgccag gact                                          24

<210> SEQ ID NO 20
<211> LENGTH: 24
<212> TYPE: DNA
<213> ORGANISM: artificial
<220> FEATURE:
<223> OTHER INFORMATION: amplification primer

<400> SEQUENCE: 20
accaaaggaa agccagccag tcta                                          24

<210> SEQ ID NO 21
<211> LENGTH: 24
<212> TYPE: DNA
<213> ORGANISM: artificial
<220> FEATURE:
<223> OTHER INFORMATION: amplification primer

<400> SEQUENCE: 21
actccacagc tcccaagcat acaa                                          24

<210> SEQ ID NO 22
<211> LENGTH: 24
<212> TYPE: DNA
<213> ORGANISM: artificial
<220> FEATURE:
<223> OTHER INFORMATION: amplification primer

<400> SEQUENCE: 22
tcccagctct ctctcttgca tctt                                          24

<210> SEQ ID NO 23
<211> LENGTH: 24
<212> TYPE: DNA
<213> ORGANISM: artificial
<220> FEATURE:
<223> OTHER INFORMATION: amplification primer

<400> SEQUENCE: 23
agtgaagctg gtgtatgcag aggt                                          24

<210> SEQ ID NO 24
<211> LENGTH: 22
<212> TYPE: DNA

```
<213> ORGANISM: artificial
<220> FEATURE:
<223> OTHER INFORMATION: amplification primer

<400> SEQUENCE: 24
agagggctgc tttatgcagg tg                                              22

<210> SEQ ID NO 25
<211> LENGTH: 25
<212> TYPE: DNA
<213> ORGANISM: artificial
<220> FEATURE:
<223> OTHER INFORMATION: amplification primer

<400> SEQUENCE: 25
ctacatttgg gtctttgctg ccatg                                           25

<210> SEQ ID NO 26
<211> LENGTH: 17
<212> TYPE: DNA
<213> ORGANISM: artificial
<220> FEATURE:
<223> OTHER INFORMATION: amplification primer

<400> SEQUENCE: 26
agcagcccca ggcagat                                                    17

<210> SEQ ID NO 27
<211> LENGTH: 22
<212> TYPE: DNA
<213> ORGANISM: artificial
<220> FEATURE:
<223> OTHER INFORMATION: amplification primer

<400> SEQUENCE: 27
cggagaggac ggtcacgttt ac                                              22

<210> SEQ ID NO 28
<211> LENGTH: 23
<212> TYPE: DNA
<213> ORGANISM: artificial
<220> FEATURE:
<223> OTHER INFORMATION: amplification primer

<400> SEQUENCE: 28
gtccagcact agtgatcttg tcc                                             23

<210> SEQ ID NO 29
<211> LENGTH: 24
<212> TYPE: DNA
<213> ORGANISM: artificial
<220> FEATURE:
<223> OTHER INFORMATION: amplification primer

<400> SEQUENCE: 29
cgtgggagtt ttgaaatgcg atgt                                            24

<210> SEQ ID NO 30
<211> LENGTH: 18
<212> TYPE: DNA
<213> ORGANISM: artificial
<220> FEATURE:
<223> OTHER INFORMATION: amplification primer

<400> SEQUENCE: 30
cctgtctctg ctcctgcg                                                   18
```

```
<210> SEQ ID NO 31
<211> LENGTH: 20
<212> TYPE: DNA
<213> ORGANISM: artificial
<220> FEATURE:
<223> OTHER INFORMATION: amplification primer

<400> SEQUENCE: 31
tgcacacatg cacagtggag                                                     20

<210> SEQ ID NO 32
<211> LENGTH: 20
<212> TYPE: DNA
<213> ORGANISM: artificial
<220> FEATURE:
<223> OTHER INFORMATION: amplification primer

<400> SEQUENCE: 32
ctccaaggtt ctgcagcctc                                                     20

<210> SEQ ID NO 33
<211> LENGTH: 24
<212> TYPE: DNA
<213> ORGANISM: artificial
<220> FEATURE:
<223> OTHER INFORMATION: amplification primer

<400> SEQUENCE: 33
ggtatgacta cacattcagg ctgg                                                24

<210> SEQ ID NO 34
<211> LENGTH: 22
<212> TYPE: DNA
<213> ORGANISM: artificial
<220> FEATURE:
<223> OTHER INFORMATION: amplification primer

<400> SEQUENCE: 34
gtggtacata gtgcatggtc cg                                                  22

<210> SEQ ID NO 35
<211> LENGTH: 24
<212> TYPE: DNA
<213> ORGANISM: artificial
<220> FEATURE:
<223> OTHER INFORMATION: amplification primer

<400> SEQUENCE: 35
ggcgacatac cccaacttca taag                                                24

<210> SEQ ID NO 36
<211> LENGTH: 22
<212> TYPE: DNA
<213> ORGANISM: artificial
<220> FEATURE:
<223> OTHER INFORMATION: amplification primer

<400> SEQUENCE: 36
cgttcttagg accaaagggc tg                                                  22

<210> SEQ ID NO 37
<211> LENGTH: 21
<212> TYPE: DNA
<213> ORGANISM: artificial
<220> FEATURE:
<223> OTHER INFORMATION: amplification primer
```

```
<400> SEQUENCE: 37
ccagcatcca tgtctctgca c                                              21

<210> SEQ ID NO 38
<211> LENGTH: 15
<212> TYPE: DNA
<213> ORGANISM: artificial
<220> FEATURE:
<223> OTHER INFORMATION: amplification primer

<400> SEQUENCE: 38
gcccagagcg cctga                                                     15

<210> SEQ ID NO 39
<211> LENGTH: 17
<212> TYPE: DNA
<213> ORGANISM: artificial
<220> FEATURE:
<223> OTHER INFORMATION: amplification primer

<400> SEQUENCE: 39 ccagccctg gaccact                                                    17
```

METHODS OF AMPLIFYING WHOLE GENOME OF A SINGLE CELL

RELATED APPLICATION DATA

This application is a National Stage Application under 35 U.S.C. 371 of co-pending PCT application PCT/US2012/038930 designating the United States and filed May 22, 2012; which claims the benefit of provisional application No. 61/621,271 and filed Apr. 6, 2012; which claims the benefit of provisional application No. 61/550,677 and filed Oct. 24, 2011; which claims the benefit of provisional application No. 61/510,539 and filed Jul. 22, 2011; which claims the benefit of provisional application No. 61/490,790 and filed May 27, 2011 each of which are hereby incorporated by reference in their entireties.

STATEMENT OF GOVERNMENT INTERESTS

This invention was made with government support under 3R01HG005097-02 and 3R01HG005097-02S1 from the National Institute of Health. The Government has certain rights in the invention.

BACKGROUND

Field of the Invention

Embodiments of the present invention relate in general to methods and compositions for amplifying genomic sequences, such as the whole genome of a single cell.

Description of Related Art

Formation of primer dimers is a common problem in existing methods for DNA or RNA amplification using random primers. In order to achieve efficient priming for each individual sequence, random primers must be applied at very high concentrations. The efficiency of annealing to a specific target DNA or RNA template or the entire population of template molecules is greatly reduced by the formation of primer-dimers resulting from the high primer concentrations required for efficient priming. Other problems known in the art when using random primers to amplify DNA include an inability to amplify the genome in its entirety due to locus dropout (loss), generation of short amplification products, and in some cases, the inability to amplify degraded or artificially fragmented DNA.

Methods directed to aspects of whole genome amplification are reported in the literature. See, for example, U.S. Pat. No. 7,718,403, US 2003/0108870 and U.S. Pat. No. 7,402,386. PCR-based methods such as GenomePlex and Picoplex can induce significant amplification bias across different loci in the genome which results in significant amplification loci dropout. With these methods, only 5-30% of the genome is often sequenced with reasonable sequencing depth from amplified single cells. Multiple displacement amplification utilizes low temperature amplification which leads to large amounts of chimera sequences that do not belong to the original genome resulting in significant false discovery rate of one out of several kilobases and introduces artifacts into the whole genome sequencing analysis. While methods for whole genome amplification have been proposed, such methods can generally be inefficient, complex and expensive. Therefore, a need exists for alternate methods of amplifying small amounts of genomic DNA, such as from a single cell or small group of cells.

SUMMARY

Embodiments of the present disclosure are directed to a method of amplifying DNA such as a small amount of genomic DNA or a limited amount of DNA such as a genomic sequence or genomic sequences obtained from a single cell or a plurality of cells of the same cell type or from a tissue, fluid or blood sample obtained from an individual or a substrate. According to certain aspects of the present disclosure, the methods described herein can be performed in a single tube with a single reaction mixture and programmable thermocycles. The methods described herein can provide substantial coverage of the entire genome of a single cell producing amplified DNA for high-throughput sequencing.

According to an additional aspect, methods are provided herein for performing whole genome amplification of single cells with high fidelity and amplification uniformity or coverage across different loci in the genome which is useful for further sequencing or analysis using high throughput sequencing platforms known to those of skill in the art. Methods provided herein minimize amplification bias and provide substantially complete or complete genome coverage of DNA sequencing of genomic DNA from a single cell. Methods described herein can amplify greater than 90 percent of genomic DNA from a single cell while greater than 70 percent or 75 percent of the genomic DNA can be sequenced with a sequencing depth of 7× or 10× or 15× with little, substantially few or no chimera sequences. Methods described herein reduce or eliminate creation of sequencing artifacts and facilitate advanced genomic analysis of single nucleotide polymorphisms, copy number variations and structural variations. Methods described herein have particular application in biological systems or tissue samples characterized by highly heterogenous cell populations such as tumor and neural masses. Methods described herein to amplify genomic DNA facilitate the analysis of such amplified DNA using next generation sequencing techniques known to those of skill in the art and described herein.

According to one aspect, primers are used where each primer includes a common sequence, a variable sequence and a fixed sequence. After double stranded DNA is denatured into single stranded DNA, the primers are annealed to the ssDNA at a first low temperature followed by amplification at a higher temperature in the presence of at least one of a strand displacing polymerase or polymerases with 5' to 3' exonuclease activity. According to one aspect, several thermocycles take place to amplify the DNA. At the end of the second thermocycle, where double stranded DNA including primer sequences and sequences complementary thereto at each end is denatured at a given temperature, the temperature of the reaction mixture is reduced to a temperature at which free primers hybridize to the 3' end of the single stranded amplicon. This inhibits the amplicon from binding to itself or other amplicons as a result of a primer sequence being at one end of the amplicon and a sequence complementary to the primer sequence being at the other end of the amplicon. The temperature of the reaction mixture is then lowered to a low temperature where annealing of primers occurs to the single stranded DNA and then another amplification cycle takes place.

The DNA amplification methods of the present disclosure will be useful for amplifying small or limited amounts of DNA, which will allow multiple sites in the DNA sample to be genotyped for high-throughput screening. Additionally, the present method will allow for the rapid construction of band specific painting probes for any chromosomal region, and can also be used to microdissect and amplify unidentifiable chromosomal regions or marker chromosomes in abnormal karyotypes. The presently disclosed method will also allow for the rapid cloning of amplified DNA for sequencing or generating DNA libraries. Thus, the method will not only be a valuable tool for genotype analysis and high-throughput screening, it should also be a valuable tool in cytogenetic diagnosis.

Embodiments described herein utilize non-standard PCR cycles to perform whole genome amplification from a single mammalian cell. Certain polymerases provide exemplary results. A step may be provided during cycling to anneal a free primer to a complementary primer sequence on an amplicon, such as at the 3' end of the amplicon, thereby preventing hybridization within the amplicon, i.e. hybridizing with itself, or between amplicons, such as to form chimeras. Procedures are described for removing primer sequences on either ends of the amplicons generated using the methods described herein.

According to an additional aspect of the present disclosure, methods are provided for processing at least one cell, one or more cells, or a plurality of cells, such as two or more cells for example for nucleic acid amplification according to the methods described herein, as well as, nucleic acid amplification methods known to those of skill in the art. According to an exemplary embodiment, a single cell is isolated and then lysed in a volume of fluid to obtain the genomic DNA of the cell. The volume of fluid is then separated into two or more or a plurality of sub-volumes of fluid using methods known to those of skill in the art resulting in a portion of the genomic DNA from the single cell being in one or more of the plurality of sub-volumes. The number of resulting sub volumes can range from between about 2 to about 100,000, between about 2 to about 10,000, between about 2 to about 1,000, between about 2 to about 500, between about 2 to about 100, between about 2 to about 50, between about 2 to about 25, between about 2 to about 12, between about 2 to about 10 or any range of value in between whether overlapping or not. According to one aspect, the separation method results in two homologue alleles being in different sub-volumes. According to this aspect, two homologue alleles are separated by separating the volume of genomic DNA into separate sub-volumes. The greater the number of sub-volumes, the greater the likelihood that two homologue alleles will be in different sub-volumes. The two homologue alleles being in different sub-volumes allows the haplotyping of the genomic DNA. According to one aspect, one or more or all of the sub-volumes are equal in volume. According to an additional aspect, a portion of the genomic DNA from the single cell is in each sub-volume of fluid. According to a further aspect, the portion of the genomic DNA in a sub-volume of fluid is then amplified to produce an amplified portion of the genomic DNA. According to one aspect, each portion of genomic DNA in a sub-volume of fluid is amplified to produce an amplified portion of genomic DNA. According to a still further aspect, one or more amplified portions of the genomic DNA is sequenced to produce sequenced DNA. According to a still further aspect, the sequenced DNA is analyzed, for example, using methods known to those of skill in the art. It is to be understood that two or more cells can be processed in the same manner as a single cell. For example, two or more cells are isolated and placed within a single volume of fluid. The two or more cells are lysed and the genomic DNA from the two or more cells is within the volume of fluid. The volume of fluid is then separated into two or more or a plurality of sub-volumes of fluid using methods known to those of skill in the art resulting in a portion of the genomic DNA from the two or more cells being in one or more of the plurality of sub-volumes. According to one aspect, a portion of the genomic DNA from the two or more cells is in each sub-volume of fluid. The DNA may then be amplified, sequenced and analyzed. According to one aspect, the two or more cells are of the same cell type. Alternatively, the two or more cells can be of a different cell type. Still alternatively, the two or more cells can be of the same or different cell type.

According to one aspect, methods are provided for separating the genetic materials of an organism into portions of sub-single cell level. Once separated into sub-single cell level portions, the genetic material can be amplified, sequenced and analyzed using high throughput genotyping or sequencing methods. By separating genetic material into sub-single cell portions and then amplifying, sequencing and analyzing the genetic material, methods of haplotyping diploid or polyploid cells are provided. According to an additional aspect, the methods described herein can be used for de-novo assembly of species with complex structural variations and species without a reference genome. The methods described herein can utilize varied sources of DNA materials, including genetically heterogenous tissues (e.g. cancers), rare and precious samples (e.g. embryonic stem cells), and non-dividing cells (e.g. neurons) and the like, as well as, sequencing platforms and genotyping methods known to those of skill in the art. Methods of haplotyping described herein may utilize one or more procedures known to those of skill in the art and described in each of the following references hereby incorporated herein in their entireties for all purposes: Levy, S. et al. The diploid genome sequence of an individual human. *PloS Biol.* 5, e254 (2007); de Bakker, P. I. et al. A high-resolution HLA and SNP haplotype map for disease association studies in the extended human MHC. *Nat. Genet.* 38, 1166-1172 (2006); Nagel, R. L. et al. The Senegal DNA haplotype is associated with the amelioration of anemia in African-American sickle cell anemia patients. *Blood* 77, 1371-1375 (1991); Drysdale, C. M. et al. Complex promoter and coding region beta 2-adrenergic receptor haplotypes alter receptor expression and predict in vivo responsiveness. *Proc. Natl. Acad. Sci. USA* 97, 10483-10488 (2000); Sun, T. et al. Haplotypes in matrix metalloproteinase gene cluster on chromosome 11q22 contribute to the risk of lung cancer development and progression. *Clin. Cancer Res.* 12, 7009-7017 (2006); Wang, J. et al. The diploid genome sequence of an Asian individual. *Nature* 456, 60-65 (2008); Kitzman, J. O. et al. Haplotype-resolved genome sequencing of a Gujarati Indian individual. *Nat. Biotech.* 29, 59-63 (2011); International HapMap Consortium. Integrating common and rare genetic variation in diverse human populations. *Nature* 467, 52-58 (2010); Xiao, M. et. al. Direct determination of haplotypes from single DNA molecules. *Nat. Methods* 6, 199-201 (2009); and Fan H. C. et al. Whole-genome molecular haplotyping of single cells. *Nat. Biotech.* 29, 51-57 (2011).

Further features and advantages of certain embodiments of the present disclosure will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
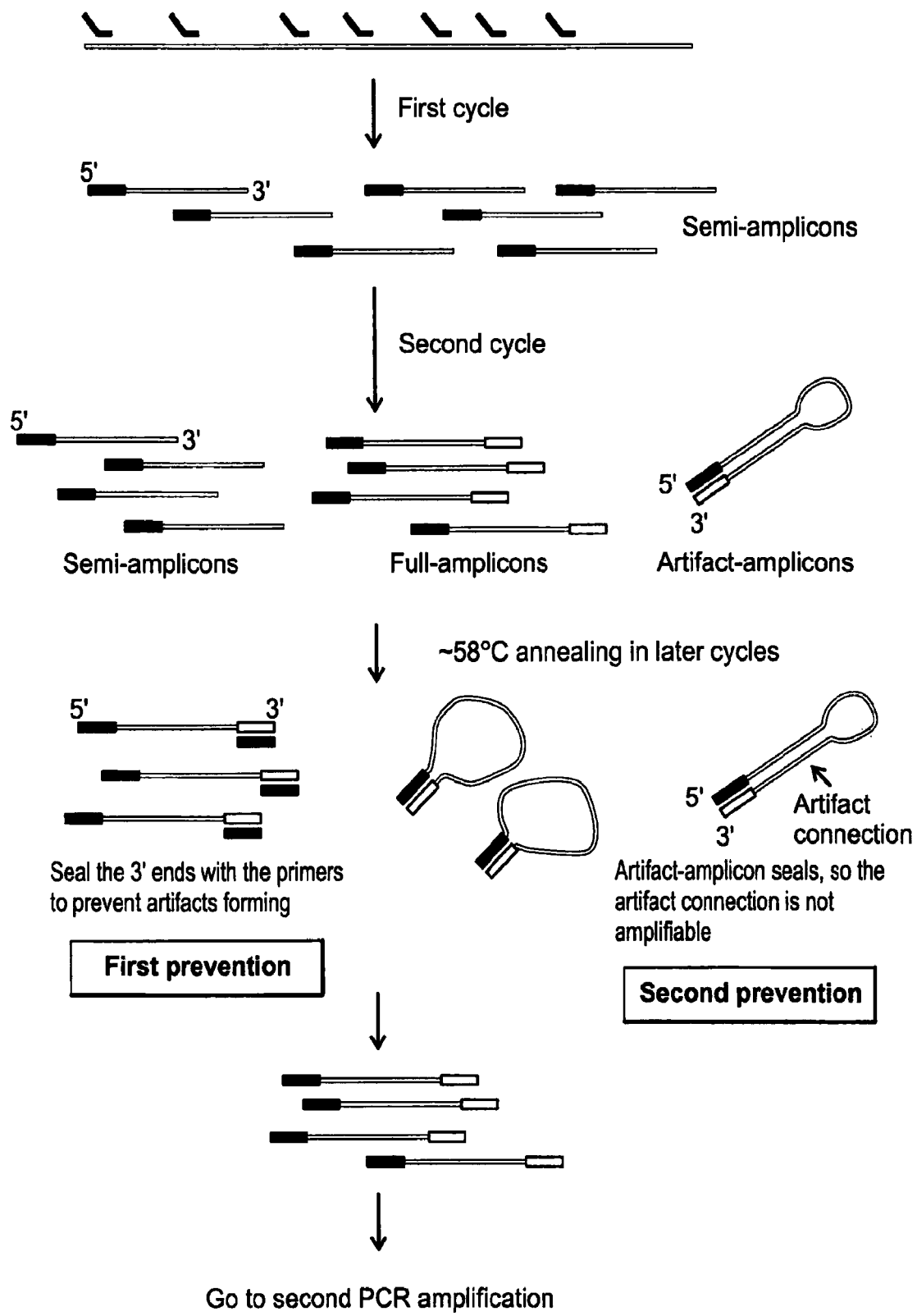
FIG. 1 is a schematic depicting an embodiment of the method of amplifying DNA described herein.
Figure 2:
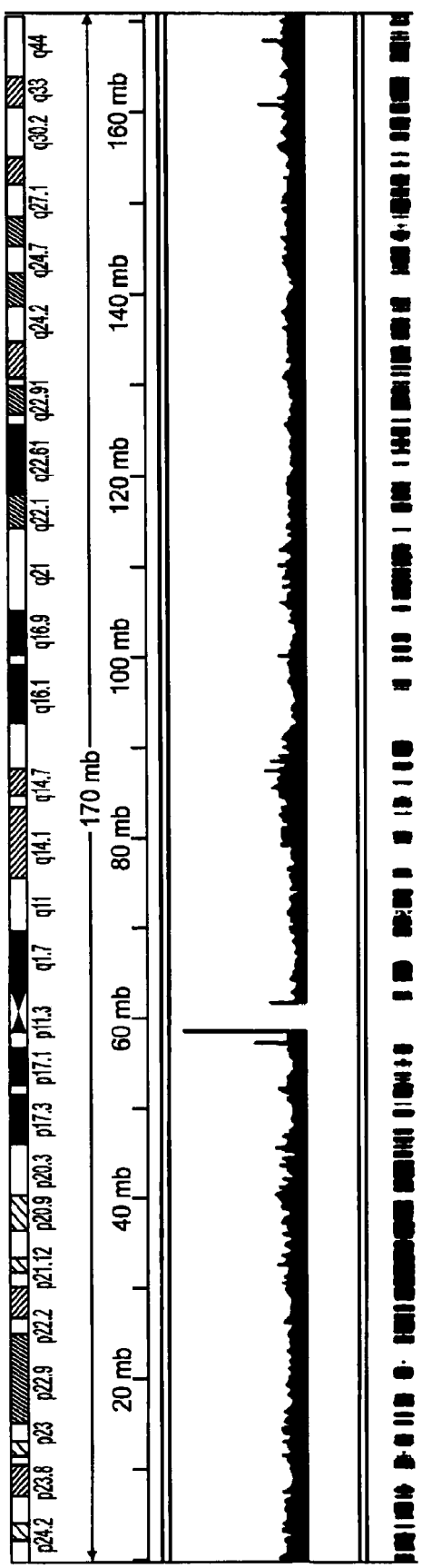
FIG. 2 is a histogram of sequencing data showing coverage of genomic data from a single cell for a sequencing depth of 15× and where the histogram is linear scale.
Figure 2A:
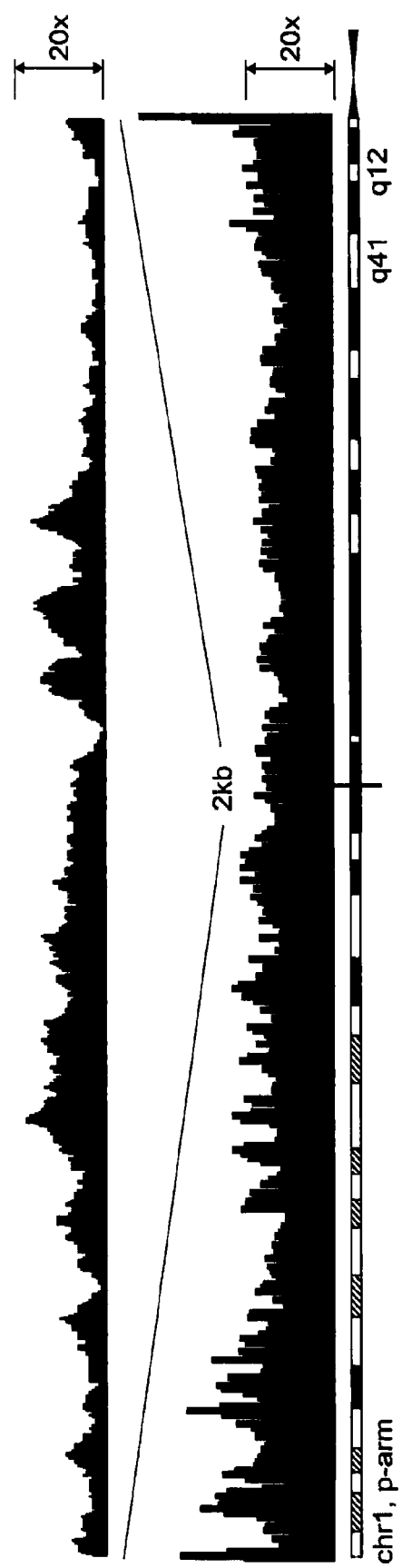
FIG. 2A is a histogram of sequencing data showing coverage of genomic data from a single cell over the entirety of chromosome 1 of a single cell and zooming into a 2 kilobase region (inset).

The practice of certain embodiments or features of certain embodiments may employ, unless otherwise indicated, conventional techniques of molecular biology, microbiology, recombinant DNA, and so forth which are within ordinary skill in the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coli- gan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

The present invention is based in part on the discovery of methods for amplifying DNA or RNA (such as mRNA), such as a genome or transcriptome or both. Such DNA or RNA may be obtained from a single cell or a small population of cells of the same cell type. Methods described herein allow DNA to be amplified from any species or organism in a reaction mixture, such as a single reaction mixture carried out in a single PCR tube. According to alternate aspects, the DNA may be separated into one or more separate containers or tubes or regions using pipettes or microfluidic devices and methods known to those of skill in the art such that the container or tube or region includes a portion of the DNA. The portion of DNA represents a sub-cell level of genomic DNA, i.e. a portion of the genomic DNA extracted from the cell which may be the total amount of genomic DNA in the cell. Amplification methods described herein or amplification methods known to those of skill in the art can then be used to amplify the portions of DNA in the container, tube or region. In one aspect, methods described herein include sequence independent amplification of DNA from any source including but not limited to human, animal, plant, yeast, viral, eukaryotic and prokaryotic DNA.

In a particular aspect, embodiments are directed to methods for the amplification of substantially the entire genome or entire transcriptome without loss of representation of specific sites (herein defined as "whole genome amplification" and "whole transcriptome amplification", respectively). In a specific embodiment, whole genome amplification comprises simultaneous amplification of substantially all fragments of a genomic library. In a further specific embodiment, "substantially entire" or "substantially all" refers to about 80%, about 85%, about 90%, about 95%, about 97%, or about 99% of all sequence in a genome. A skilled artisan recognizes that amplification of the whole genome will, in some embodiments, comprise non-equivalent amplification of particular sequences over others.

In one aspect, embodiments provide a two-step procedure that can be performed in a single tube or in a micro-titer plate, for example, in a high throughput format. The first step involves production of a library of amplicons using primers having a common sequence, a variable sequence and a fixed sequence and at least one enzyme possessing strand-displacement activity or exonuclease activity. The method includes the post-annealing step of annealing a free primer to one end of an amplicon to inhibit hybridization within the amplicon or between amplicons such that further thermocycling produces amplification where PCR bias is reduced. The combination of the primers used and the post annealing step maximizes coverage of the entire genome. The resulting library of molecules are then amplified in a second step by standard amplification methods such as PCR using, for example, Taq polymerase and a primer corresponding to the known sequence, resulting in several thousand-fold amplification of the entire genome or transcriptome without significant bias: The products of this amplification can be re-amplified additional times, resulting in amplification that exceeds, for example, several million fold.

According to certain aspects, the DNA sample in the reaction mixture is subjected to DNA amplification by at least one DNA polymerase, wherein the primers anneal to the DNA to allow the DNA polymerase to synthesize a complementary DNA strand from the 3' end of the primer to produce a DNA product. The steps for DNA amplification by the DNA polymerase are denaturing the DNA product; annealing the primers to the DNA to form a DNA-primer hybrid; and incubating the DNA-primer hybrid in the presence of nucleobases to allow the DNA polymerase to extend the primer and synthesize the DNA product.

According to a general aspect, a first set DNA amplification begins by denaturing the double-stranded DNA sample to a single-stranded condition, which allows primers to anneal to the DNA. Next, the reaction temperature is lowered to a temperature that allows random nucleotides at the 3' end of the first primer to anneal to the DNA to form hybrid duplexes. After the hybrid duplexes form, one or more DNA polymerases present in the reaction mixture extends the complementary DNA strand from the 3' end of the first primer during an incubation period. A DNA polymerase may have 5' to 3' exonuclease activity or strand displacement activity.

After the first cycle of DNA amplification described above, the newly synthesized complementary DNA strand will have the generic sequence of the first primer at its 5' end, which was incorporated into the strand when the 3' end of the first primer was used as the starting point for synthesizing the complementary DNA strand. The above steps of denaturation, annealing, and extension can be repeated, and generally should be repeated at least once during the first set of reactions. The denaturation step of the second cycle of the first set of reactions separates the new first cycle DNA strands with the 5' generic sequence from the original DNA strands. After denaturation, the new first cycle DNA strands are available to the free primer present in the reaction mixture for another round of annealing and extension.

During the second cycle of the first set of reactions, the primers anneal to the first cycle DNA strand, DNA polymerase extends a complementary strand from the 3' end of the primer and the newly synthesized complementary DNA once again incorporates the 5' end of the primer into its sequence. This new second cycle DNA will also have the reverse complement of the primer sequence on its 3' end, because the DNA polymerase will synthesize the full length complementary DNA product of the first cycle DNA strand, which has the primer sequence at its 5' end. Thus, the amplified DNA resulting from the second and subsequent cycles has the primer sequence at one end of the DNA and its reverse complement at the other end. According to one aspect, the DNA is subjected to conditions such that free primer hybridizes to the complementary primer sequence at the 3' end which prevents hybridization of the two ends within the same amplicon or hybridization with other amplicons.

In a preferred embodiment, the DNA sample is genomic DNA, microdissected chromosome DNA, yeast artificial chromosome (YAC) DNA, cosmid DNA, phage DNA, P1 derived artificial chromosome (PAC) DNA, or bacterial artificial chromosome (BAC) DNA. In another preferred embodiment, the DNA sample is mammalian DNA, plant DNA, yeast DNA, viral DNA, or prokaryotic DNA. In yet another preferred embodiment, the DNA sample is obtained from a human, bovine, porcine, ovine, equine, rodent, avian, fish, shrimp, plant, yeast, virus, or bacteria. Preferably the DNA sample is genomic DNA, wherein the method of amplifying DNA includes DNA amplification with a fluorescent label.

According to one aspect, primers are used where each primer includes a common sequence (also known as a constant sequence), a variable sequence and a fixed sequence. In certain embodiments, the primers may be referred to as quasi-degenerated primers. The primers can initiate overlapping amplicons throughout the genome. The constant region and a variable region include a nucleic acid sequence that is substantially non-self-complementary and substantially non-complementary to other primers in the plurality of primers used in the reaction mixture. The constant region is preferably known and may be a targeted sequence for a primer in amplification methods. The variable region may be randomly selected or may be purposefully selected commensurate with the frequency of its representation in a source DNA, such as genomic DNA. In specific embodiments, the nucleotides of the variable region will prime at target sites in a source DNA, such as a genomic DNA, containing the corresponding Watson-Crick base partners. In a particular embodiment, the variable region is considered degenerate. According to one aspect, the common sequence of the primer is common to all primers used and is characterized by a plurality of nucleotides, such as between 10 and 30 nucleotides, which include G, T, and A, with the common sequence excluding C. That is, C is not present in the common sequence. The variable sequence is characterized by a plurality of nucleotides, such as between 3 and 7 nucleotides which are randomly selected from among G, T, A, and C. For example, if the variable sequence includes 5 nucleotides, then the number of possible random sequences forming primers is $4^5$. The fixed sequence includes or is composed of between 2 and 4 nucleotides and where the fixed sequence avoids self-complementary sequences. For example, the fixed sequence can include three G (i.e., G-G-G) or three T (i.e., T-T-T) or TTG, GAA or ATG.

Exemplary primers include 5'-GT GAG TGA TGG TTG AGG TAG TGT GGA GNNNNNGGG-3' and 5'-GT GAG TGA TGG TTG AGG TAG TGT GGA GNNNNNTTT-3'. According to one aspect, the sequence includes 5N3G and 5N3T. The pair of 5N3G and 5N3T can also be replaced by any of the following pair of 5N3G and 5N3A, 5N3C and 5N3T, 5N3C and 5N3A. According to an additional aspect, the common sequence, i.e., the sequence in front of 5N can be designed to reduce primer dimerization. According to a still additional aspect, the 3' end sequences provide both strong hybridization strength and good degeneracy for covering the whole genome more evenly. Other sequences with low propensity of forming a primer dimer can be designed and used for the common sequence before 5N3T or 5N3G.

According to one aspect, the reaction mixture forms a single stranded nucleic acid molecule/primer mixture which is a mixture comprising at least one single stranded nucleic acid molecule wherein at least one primer, as described herein, is hybridized to a region in said single stranded nucleic acid molecule. In specific embodiments, multiple degenerate primers comprise complementary sequence to at least some part of the single stranded nucleic acid molecule.

In further specific embodiments, the mixture comprises a plurality of single stranded nucleic acid molecules having multiple degenerate primers hybridized thereto. In additional specific embodiments, the single stranded nucleic acid molecule is DNA or RNA.

According to an additional aspect, a reaction mixture of the genomic sequence or genomic sequences, primers and at least one polymerase with strand displacement or 5' to 3' exonuclease is provided. Strand-displacing polymerases are polymerases that will dislocate downstream fragments as it extends. Strand displacing polymerases include Φ29 Polymerase, Bst Polymerase, Pyrophage 3173, Vent Polymerase, Deep Vent polymerase, TOPOTaq DNA polymerase, Vent (exo-) polymerase, Deep Vent (exo-) polymerase, 9° Nm Polymerase, Klenow fragment of DNA Polymerase I, MMLV Reverse Transcriptase, AMV reverse transcriptase, HIV reverse transcriptase, a mutant form of T7 phage DNA polymerase that lacks 3'-5' exonuclease activity, or a mixture thereof. One or more polymerases that possess a 5' flap endonuclease or 5'-3' exonuclease activity such as Taq polymerase, Bst DNA polymerase (full length), E. coli DNA polymerase, LongAmp Taq polymerase, OneTaq DNA polymerase or a mixture thereof may be used to remove residual bias due to uneven priming.

The reaction mixture is subjected to a plurality of thermocycles. In a particular thermocycle, the reaction mixture is subjected to a first temperature also known as an annealing temperature for a first period of time to allow for sufficient annealing of the primers to the genomic sequence or genomic sequences. According to this aspect, the primers are annealed to the genomic sequence or genomic sequences at a temperature of below about 30° C. in a first step, such as between about 0° C. and about 10° C. The reaction mixture is then subjected to a second temperature also known as an amplification temperature for a second period of time to allow for the amplification of the genomic sequence or genomic sequences. According to this aspect, the genomic sequence or genomic sequences are amplified at a temperature of above about 10° C. in a second step, such as between about 10° C. and about 65° C. One of skill will understand that the temperature at which amplification takes place will depend upon the particular polymerase used. For example, Φ29 Polymerase is fully active at about 30° C. and Bst Polymerase and pyrophage 3173 polymerase (exo-) are fully active about 62° C. The double stranded DNA is then melted at a third temperature, also known as a melting temperature for a third period of time to provide single stranded DNA amplicons which may be used as amplification template. According to this aspect, the double stranded DNA is dehybridized into single stranded DNA at a temperature of above about 90° C. in a third step, such as between about 90° C. and about 100° C. The single stranded DNA amplicon may have as part of its sequence the primer sequence used for amplification. According to a certain aspect and optionally if needed, the reaction mixture is then lowered to a fourth temperature of between about 55° C. and about 60° C. also known as an annealing temperature where free primers in the reaction mixture hybridize to the DNA amplicons thereby completing the thermocycle. An exemplary temperature is about 58° C.

According to an additional aspect of a second thermocycle, at least one of a strand displacing polymerase or polymerase with 5' to 3' exonuclease activity is added to the reaction mixture of amplicons with the hybridized primers and is then subjected to a second thermocycle similar to the first thermocycle, namely, the reaction mixture is subjected to an amplification temperature and a melting temperature. The DNA amplicons generated by the second cycle may include the primer sequence at one end of the amplicon and a sequence complementary to the primer sequence at the other end of the amplicon. Such an amplicon may be prone to the ends hybridizing to each other or to other amplicons. Accordingly, the second and subsequent thermocycles include after the melting temperature the step of hybridizing the 3' end of the amplicon with a free primer in the reaction mixture. According to a certain aspect, the reaction mixture post melting step is subjected to a temperature lower than the melting step temperature also known as a 3' end primer hybridizing temperature to allow free primer to hybridize with the 3' end of the amplicon. The reaction mixture is then lowered to the fourth temperature of the first cycle also known as an annealing temperature where free primers in the reaction mixture hybridize to the DNA amplicons thereby completing the second thermocycle. Subsequent thermocycles similar to the second thermocycle are conducted where at least one of a strand displacing nuclease or 5' to 3' exonuclease is added to the reaction mixture of amplicons with the hybridized primers and is then subjected to an amplification temperature, a melting temperature, a 3' end primer hybridizing temperature and an annealing temperature. According to one aspect, a final cycle may be conducted similar to the second cycle without subjecting the reaction mixture to the 3' end primer hybridizing temperature or the annealing temperature. In this manner, the final cycle terminates when the reaction mixture is subjected to the melting temperature to produce amplicons for further processing, amplification or sequencing. According to this aspect, the amplicons may be further processed, if in sufficient quantity, to remove the primer sequences at the 5' and 3' ends of the amplicons. According to an additional aspect, the amplicons may be amplified for example using standard PCR procedures with buffers, primers and polymerases known to those of skill in the art. According to a still additional aspect, the amplicons may be sequenced, if in sufficient quantity, using high-throughput sequencing methods known to those of skill in the art.

According to certain aspects, the DNA to be amplified in the first set of reactions is first denatured by heating the reaction mixture to between about 90° C. and about 100° C., and exemplary to about 95° C. for about 10 seconds to about five minutes and exemplary for about two minutes. During this step, both the primers are present in the reaction mixture. Alternatively, the primers can be added to the reaction mixture containing the DNA sample to be amplified before heat denaturation or at any time during the denaturation step of the first cycle of the first set of reactions.

Next, the temperature of the reaction mixture is lowered to a temperature that allows the primers to anneal to the single-stranded DNA. The annealing temperature of the random sequence of nucleotides of the first primer preferably should be between about 0° C. and about 30° C., exemplary between about 0° C. and about 10° C., for a period of about 10 seconds to about 5 minutes. Next, the reaction temperature is increased to a temperature at which the particular DNA polymerase becomes activated and begins to synthesize DNA. Different DNA polymerases may become functional at different temperatures, such that the cycle can ramp up or increase in temperature such that different DNA polymerases can be activated in series to begin to synthesize DNA. The total incubation period may be between about 2 minutes to about 7 minutes, more preferably about 5 minutes.

It is to be understood that temperatures, incubation periods and ramp times of the DNA amplification steps may vary from the values disclosed herein without significantly altering the efficiency of DNA amplification. Those of skill in the art will understand based on the present disclosure that parameters can be varied. Minor variations in reaction conditions and parameters are included within the scope of the present disclosure.

Figure 3:
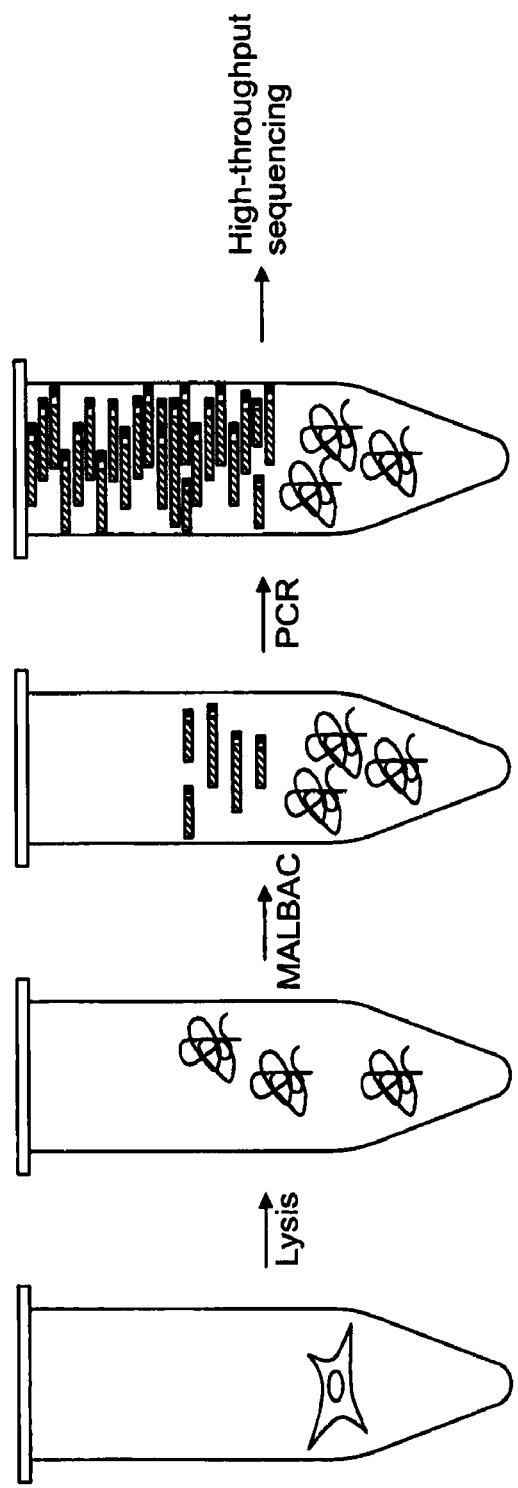
FIG. 3 is a schematic depicting general method steps of amplifying DNA described herein and including the linear pre-amplification method described herein followed by exponential amplification resulting in amplification of the genome of a cell for high-throughput sequencing and analysis.

According to certain aspects as shown in FIG. 3, a single cell is isolated and lysed to remove genomic DNA. The genomic DNA is melted into single-stranded DNA molecules. The genomic DNA is subject to conditions allowing linear pre-amplification of the genomic DNA prior to additional PCR amplification for high-throughput sequencing.

Figure 4:
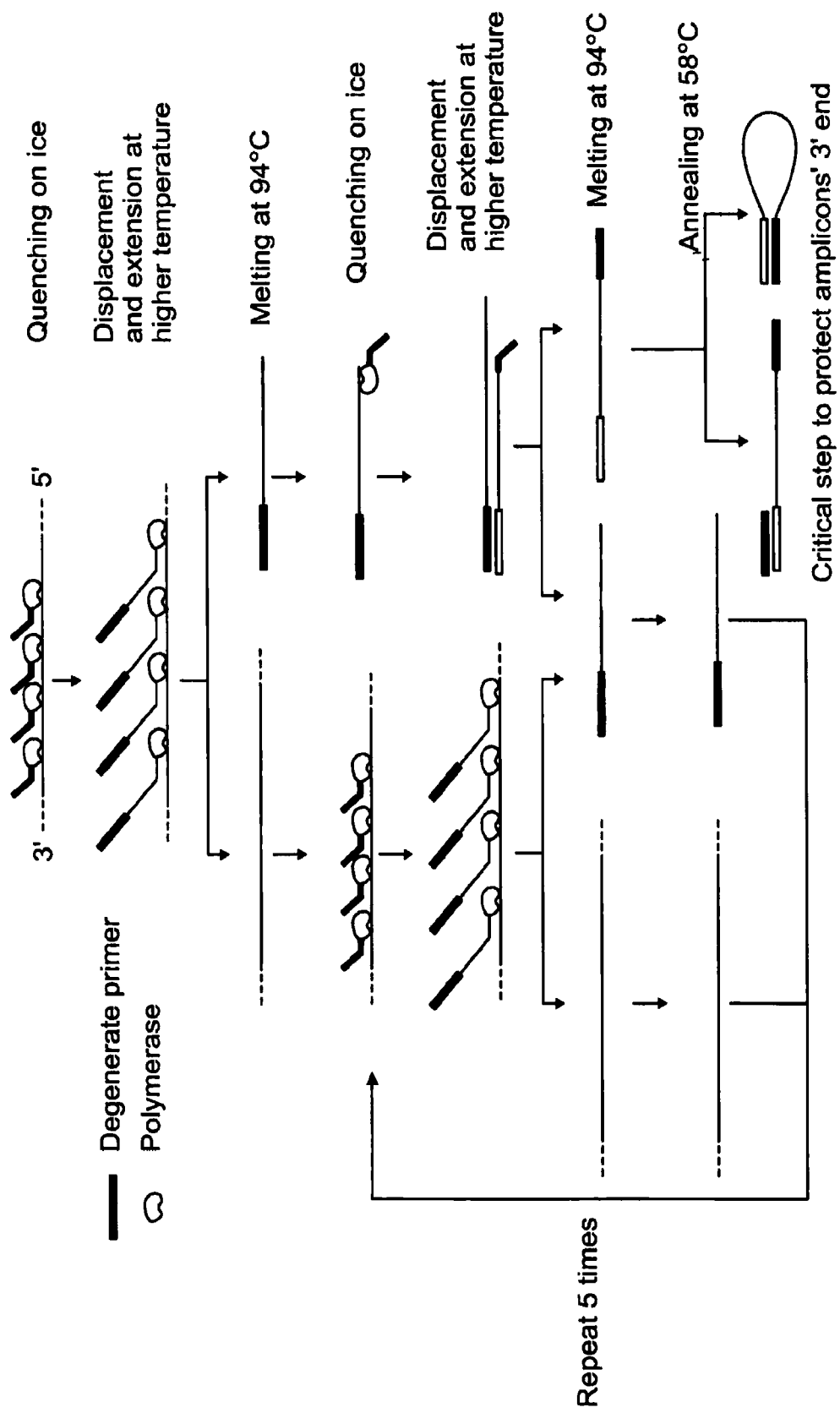
FIG. 4 is a schematic depicting multiple annealing and looping based amplification cycles (MALBAC) also referred to herein as linear pre-amplification. In a first amplification round, primers anneal randomly to single-stranded DNA molecules and are extended by a polymerase with displacement activity, which creates semi-amplicons. In a second amplification round, single stranded amplicons with complementary sequences on both ends are generated. The 3' ends are protected by loop formation at intermediate temperature, which prevents the formation of chimeras. The above cycles are repeated 4 times to generate amplicons with overlapping genome coverage that contain universal complementary sequences on both ends for subsequent PCR amplification.

According to certain aspects as shown in FIGS. 1, 3 and 4, amplification procedures described herein to amplify genomic DNA of a single cell begin with a linear pre-amplification step in which multiple annealing and looping based amplification cycles (MALBAC) are used to create overlapping shotgun amplicons covering a significant portion of the genome. After the pre-amplification step, traditional exponential amplification, such as PCR, is used to further amplify the amplicons, for example, for next generation sequencing.

According to one aspect of the present disclosure and with reference to FIGS. 1, 3 and 4, nucleic acids from a single cell, such as chromosomes, serve as templates for amplification. The genetic nucleic acids from the single cell are denatured into single strands and serve as templates. Under suitable conditions, a pool of random primers with a series of fixed bases and a series of degenerate bases hybridize at various positions along the genetic single stranded nucleic acids. Under suitable conditions, polymerases with strand displacement activity are used to generate complementary fragments of the genetic single stranded nucleic acid templates with variable lengths and beginning at random starting positions along the length of the genetic single stranded nucleic acid templates. The nucleic acids or fragments made from the genetic single stranded nucleic acid template may be referred to as first round amplicons or semi-amplicons.

Complementary fragments annealed to the genetic single stranded nucleic acid templates or to other nucleic acids present in the mixture are removed, i.e., melted or dehybridized under suitable conditions, in order to maximize the amount of single stranded nucleic acids available for hybridizing with primers and amplification. Although strand displacement polymerases may be used, the mixture may include double stranded species which are melted into single stranded species in order to maximize the amount of single stranded nucleic acids available for hybridizing with primers and amplification.

According to certain embodiments, certain first round or semi-amplicons may have enough complementarity at or near their 5' or 3' ends such that a semi-amplicon may form an artifact amplicon in the form of a loop, i.e. semi-amplicon loops. In one instance, the 5' and 3' ends are not themselves hybridized. Instead, the 5' and 3' ends remain free while a loop is formed by complementary portions of the semi-amplicon beyond the 5' and 3' ends hybridize. The amplification efficiency of semi-amplicon loops is much lower than semi-amplicons with certain semi-amplicon loops not prone to amplification as the loop seals thereby preventing amplification, even though primers may hybridize to either the 5' or 3' end. According to one embodiment, conditions are provided under which semi-amplicons form semi-amplicon loops making the semi-amplicon unavailable for amplification.

According to an additional aspect, first round amplicons, such as linear first round amplicons, are present in a mixture with the genetic single stranded nucleic acid templates. The first round amplicons serve as templates for primers in a second round of amplification along with the genetic single stranded nucleic acid templates.

Under suitable conditions, primers hybridize at various positions along the first round amplicons and the genetic single stranded nucleic acids.

Under suitable conditions, polymerases with strand displacement activity are used to generate complementary fragments of the first round amplicons with variable lengths and beginning at random starting positions along the length of the first round amplicons. The first round amplicon templates generate amplicons having complementary primer sequences at each end. Amplicons generated from first round amplicons may be referred to as second round amplicons or full amplicons. Also, polymerases with strand displacement activity are used to generate complementary fragments of the genetic single stranded nucleic acid templates with variable lengths and beginning at random starting positions along the length of the genetic single stranded nucleic acid templates. The genetic single stranded nucleic acid templates generate first round amplicons. As discussed above, certain first round amplicons may form artifact amplicons or semi-amplicon loops.

Complementary fragments annealed to the genetic single stranded nucleic acid templates or to other nucleic acids present in the mixture such as semi-amplicon templates or full amplicons are removed, i.e., melted or dehybridized under suitable conditions, in order to maximize the amount of single stranded nucleic acids available for hybridizing with primers and amplification. Although strand displacement polymerases may be used, the mixture may include double stranded species which are melted into single stranded species in order to maximize the amount of single stranded nucleic acids available for hybridizing with primers and amplification.

In order to lower artifacts or chimeras created by the 3' end of the full amplicon binding to the 5' end of a different full amplicon or other nucleic acid, the mixture is subject to conditions whereby the complementary opposite ends of the second round amplicons hybridize or anneal to one another forming a loop which makes the second round amplicons unavailable to generate chimeras or other undesirable artifacts or otherwise be used as a template under amplification conditions. Alternatively, excess primer in the mixture can hybridize or anneal under suitable conditions to the 3' end of the second round amplicons thereby maintaining a linear structure and making the second round or full amplicons unavailable to generate chimeras or otherwise be used as a template under amplification conditions. According to one aspect, the conditions promote selective hybridization of the complementary 5' and 3' ends of a full amplicon and/or selective hybridization of free primer to the 3' end of a full amplicon. The conditions do not otherwise promote the hybridization of free primer along the length of the genomic DNA, semi-amplicons or full amplicons as the free primers are not in general fully complementary to sequences along the length of the genomic DNA, semi-amplicons or full amplicons. The present disclosure takes advantage of the complementarity of the 5' and 3' ends of a full amplicon to reduce undesirable artifacts or chimeras by rendering the full amplicon unavailable for further amplification while genomic DNA and semi-amplicons are available for further amplification in the same reaction mixture.

To begin an additional round of amplification, the reaction mixture is subject to suitable conditions where primers hybridize at various positions along the first round amplicons and the genetic single stranded nucleic acids under suitable conditions while the second round amplicons or full amplicons are rendered unavailable or not prone to further amplification because of primer hybridization to the 3' end of the full amplicon or because the 5' end and the 3' end of the amplicon have hybridized together forming a loop structure. The mixture is then subjected to suitable amplification conditions whereby genomic DNA and semi-amplicons are amplified to generate semi-amplicons and full amplicons, respectively and followed by suitable looping or annealing conditions for second round or full amplicons. The cycle can be repeated as often as desired.

According to one aspect, the method of amplifying DNA further includes genotype analysis of the amplified DNA product. Alternatively, the method of amplifying DNA preferably further includes identifying a polymorphism such as a single nucleotide polymorphism (SNP) in the amplified DNA product. In preferred embodiments, a SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization. Preferably the identified SNP is associated with a phenotype, including disease phenotypes and desirable phenotypic traits. The amplified DNA generated by using the disclosed method of DNA amplification may also preferably be used to generate a DNA library, including but not limited to genomic DNA libraries, microdissected chromosome DNA libraries, BAC libraries, YAC libraries, PAC libraries, cDNA libraries, phage libraries, and cosmid libraries.

The term "genome" as used herein is defined as the collective gene set carried by an individual, cell, or organelle. The term "genomic DNA" as used herein is defined as DNA material comprising the partial or full collective gene set carried by an individual, cell, or organelle. The term "transcriptome" as used herein is defined as the collective RNA set expressed within a cell.

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide," "oligonucleotide" and "nucleic acid molecule" are used interchangeably herein and refer to a polymer of nucleotides, either deoxyribonucleotides or ribonucleotides, of any length joined together by a phosphodiester linkage between 5' and 3' carbon atoms. Polynucleotides can have any three-dimensional structure and can perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. The term also refers to both double- and single-stranded molecules. Unless otherwise specified or required, any embodiment of this invention that comprises a polynucleotide encompasses both the double-stranded form and each of two complementary single-stranded forms known or predicted to make up the double-stranded form. A polynucleotide is composed of a specific sequence of four nucleotide bases: adenine (A); cytosine (C); guanine (G); thymine (T); and uracil (U) for thymine when the polynucleotide is RNA. Thus, the term polynucleotide sequence is the alphabetical representation of a polynucleotide molecule. This alphabetical representation can be input into databases in a computer having a central processing unit and used for bioinformatics applications such as functional genomics and homology searching.

The terms "RNA," "RNA molecule" and "ribonucleic acid molecule" refer to a polymer of ribonucleotides. The terms "DNA," "DNA molecule" and "deoxyribonucleic acid molecule" refer to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In certain exemplary embodiments, an siRNA comprises between about 15-30 nucleotides or nucleotide analogs, between about 16-25 nucleotides (or nucleotide analogs), between about 18-23 nucleotides (or nucleotide analogs), and even between about 19-22 nucleotides (or nucleotide analogs) (e.g., 19, 20, 21 or 22 nucleotides or nucleotide analogs). The term "short" siRNA refers to an siRNA comprising about 21 nucleotides (or nucleotide analogs), for example, 19, 20, 21 or 22 nucleotides. The term "long" siRNA refers to an siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

As used herein, the term "isolated RNA" (e.g., "isolated mRNA") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the terms "complementary" and "complementarity" are used in reference to nucleotide sequences related by the base-pairing rules. For example, the sequence 5'-AGT-3' is complementary to the sequence 5'-ACT-3'. Complementarity can be partial or total. Partial complementarity occurs when one or more nucleic acid bases is not matched according to the base pairing rules. Total or complete complementarity between nucleic acids occurs when each and every nucleic acid base is matched with another base under the base pairing rules. The degree of complementarity between nucleic acid strands has significant effects on the efficiency and strength of hybridization between nucleic acid strands.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency. When used in reference to a single-stranded nucleic acid sequence, the term "substantially homologous" refers to any probe which can hybridize to the single-stranded nucleic acid sequence under conditions of low stringency.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman (1981) *Adv. Appl. Math.* 2:482) by the homology alignment algorithm of Needleman and Wunsch (*J. Mol. Biol.* 48:443 (1970)), by the search for similarity method of Pearson and Lipman (*Proc. Natl. Acad. Sci. USA* 85:2444 (1988)]), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I)

occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the melting temperature of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See, e.g., Anderson and Young, Quantitative Filter Hybridization, in *Nucleic Acid Hybridization* (1985)). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted.

"Low stringency conditions," when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$(H$_2$O) and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

"Medium stringency conditions," when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$ (H$_2$O) and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions," when used in reference to nucleic acid hybridization, comprise conditions equivalent to binding or hybridization at 42° C. in a solution consisting of 5×SSPE (43.8 g/l NaCl, 6.9 g/l NaH$_2$PO$_4$(H$_2$O) and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target molecule (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

In certain exemplary embodiments, cells are identified and then a single cell or a plurality of cells are isolated. Cells within the scope of the present disclosure include any type of cell where understanding the DNA or RNA content is considered by those of skill in the art to be useful. A cell according to the present disclosure includes a cancer cell of any type, hepatocyte, oocyte, embryo, stem cell, iPS cell, ES cell, neuron, erythrocyte, melanocyte, astrocyte, germ cell, oligodendrocyte, kidney cell and the like. According to one aspect, the methods of the present invention are practiced with the cellular RNA or cellular DNA from a single cell. A plurality of cells includes from about 2 to about 1,000,000 cells, about 2 to about 10 cells, about 2 to about 100 cells, about 2 to about 1,000 cells, about 2 to about 10,000 cells, about 2 to about 100,000 cells, about 2 to about 10 cells or about 2 to about 5 cells.

Nucleic acids processed by methods described herein may be DNA, RNA, or DNA-RNA chimeras, and they may be obtained from any useful source, such as, for example, a human sample. In specific embodiments, a double stranded DNA molecule is further defined as comprising a genome, such as, for example, one obtained from a sample from a human. The sample may be any sample from a human, such as blood, serum, plasma, cerebrospinal fluid, cheek scrapings, nipple aspirate, biopsy, semen (which may be referred to as ejaculate), urine, feces, hair follicle, saliva, sweat, immunoprecipitated or physically isolated chromatin, and so forth. In specific embodiments, the sample comprises a single cell.

In particular embodiments, the amplified nucleic acid molecule from the sample provides diagnostic or prognostic information. For example, the prepared nucleic acid molecule from the sample may provide genomic copy number and/or sequence information, allelic variation information, cancer diagnosis, prenatal diagnosis, paternity information, disease diagnosis, detection, monitoring, and/or treatment information, sequence information, and so forth.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. Furthermore, in general, cells from any population can be used in the methods, such as a population of prokaryotic or eukaryotic single celled organisms including bacteria or yeast. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, such that each single cell is placed in a single well.

Methods for manipulating single cells are known in the art and include fluorescence activated cell sorting (FACS), flow cytometry (Herzenberg., PNAS USA 76:1453-55 1979), micromanipulation and the use of semi-automated cell pickers (e.g. the Quixell™ cell transfer system from Stoelting Co.). Individual cells can, for example, be individually selected based on features detectable by microscopic observation, such as location, morphology, or reporter gene expression. Additionally, a combination of gradient centrifugation and flow cytometry can also be used to increase isolation or sorting efficiency.

Once a desired cell has been identified, the cell is lysed to release cellular contents including DNA and RNA, using methods known to those of skill in the art. The cellular contents are contained within a vessel. In some aspects of the invention, cellular contents, such as genomic DNA and RNA, can be released from the cells by lysing the cells. Lysis can be achieved by, for example, heating the cells, or by the use of detergents or other chemical methods, or by a combination of these. However, any suitable lysis method known in the art can be used. A mild lysis procedure can advantageously be used to prevent the release of nuclear chromatin. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., *Neurosci Res* 60(4):439-51 (2008)); or 70° C. for 90 seconds in PCR buffer II (Applied Biosystems) supplemented with 0.5% NP-40 (Kurimoto et al., *Nucleic Acids Res* 34(5):e42 (2006)); or lysis can be achieved with a protease such as Proteinase K or by the use of chaotropic salts such as guanidine isothiocyanate (U.S. Publication No. 2007/0281313). Amplification of genomic DNA according to methods described herein can be performed directly on cell lysates, such that a reaction mix can be added to the cell lysates. Alternatively, the cell lysate can be separated into two or more volumes such as into two or more containers, tubes or regions using methods described herein or methods known to those of skill in the art with a portion of the cell lysate contained in each volume container, tube or region. Genomic DNA contained in each container, tube or region may then be amplified by methods described herein or methods known to those of skill in the art.

A nucleic acid used in the invention can also include native or non-native bases. In this regard a native deoxyribonucleic acid can have one or more bases selected from the group consisting of adenine, thymine, eytosine or guanine and a ribonucleic acid can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

As used herein, the term "primer" generally includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate or quasi-degenerate in sequence. Primers within the scope of the present invention bind adjacent to a target sequence. A "primer" may be considered a short polynucleotide, generally with a free 3'-OH group that binds to a target or template potentially present in a sample of interest by hybridizing with the target, and thereafter promoting polymerization of a polynucleotide complementary to the target. Primers of the instant invention are comprised of nucleotides ranging from 17 to 30 nucleotides. In one aspect, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

DNA amplified in a first step using the methods describe herein can be further amplified using methods known to those of skill in the art. In certain aspects, amplification is achieved using PCR. The term "polymerase chain reaction" ("PCR") of Mullis (U.S. Pat. Nos. 4,683,195, 4,683,202, and 4,965,188) refers to a method for increasing the concentration of a segment of a target sequence in a mixture of nucleic acid sequences without cloning or purification. This process for amplifying the target sequence consists of introducing a large excess of two oligonucleotide primers to the nucleic acid sequence mixture containing the desired target sequence, followed by a precise sequence of thermal cycling in the presence of a polymerase (e.g., DNA polymerase). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. Methods and kits for performing PCR are well known in the art. PCR is a reaction in which replicate copies are made of a target polynucleotide using a pair of primers or a set of primers consisting of an upstream and a downstream primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as replication. A primer can also be used as a probe in hybridization reactions, such as Southern or Northern blot analyses.

The expression "amplification" or "amplifying" refers to a process by which extra or multiple copies of a particular polynucleotide are formed. Amplification includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting amplification reaction are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification can be sequenced directly.

When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

The terms "reverse-transcriptase PCR" and "RT-PCR" refer to a type of PCR where the starting material is mRNA. The starting mRNA is enzymatically converted to complementary DNA or "cDNA" using a reverse transcriptase enzyme. The cDNA is then used as a template for a PCR reaction.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., J. Biol. Chem., 264, 8935-8940, 1989), hyperbranched rolling circle amplification (Lizard et al., Nat. Genetics, 19, 225-232, 1998), and loop-mediated isothermal amplification (Notomi et al., Nuc. Acids Res., 28, e63, 2000) each of which are hereby incorporated by reference in their entireties.

For emulsion PCR, an emulsion PCR reaction is created by vigorously shaking or stirring a "water in oil" mix to generate millions of micron-sized aqueous compartments. The DNA library is mixed in a limiting dilution either with the beads prior to emulsification or directly into the emulsion mix. The combination of compartment size and limiting dilution of beads and target molecules is used to generate compartments containing, on average, just one DNA molecule and bead (at the optimal dilution many compartments will have beads without any target) To facilitate amplification efficiency, both an upstream (low concentration, matches primer sequence on bead) and downstream PCR primers (high concentration) are included in the reaction mix. Depending on the size of the aqueous compartments generated during the emulsification step, up to $3 \times 10^9$ individual PCR reactions per µl can be conducted simultaneously in the same tube. Essentially each little compartment in the emulsion forms a micro PCR reactor. The average size of a compartment in an emulsion ranges from sub-micron in diameter to over a 100 microns, depending on the emulsification conditions.

"Identity," "homology" or "similarity" are used interchangeably and refer to the sequence similarity between two nucleic acid molecules. Identity can be determined by comparing a position in each sequence which can be aligned for purposes of comparison. When a position in the compared sequence is occupied by the same base or amino acid, then the molecules are homologous at that position. A degree of identity between sequences is a function of the number of matching or identical positions shared by the sequences. An unrelated or non-homologous sequence shares less than 40% identity, or alternatively less than 25% identity, with one of the sequences of the present invention.

A polynucleotide has a certain percentage (for example, 60%, 65%, 70%, 75%, 80%, 85%, 90%, 95%, 98% or 99%) of "sequence identity" to another sequence means that, when aligned, that percentage of bases are the same in comparing the two sequences. This alignment and the percent sequence identity or homology can be determined using software programs known in the art, for example those described in Ausubel et al., Current Protocols in Molecular Biology, John Wiley & Sons, New York, N.Y., (1993). Preferably, default parameters are used for alignment. One alignment program is BLAST, using default parameters. In particular, programs are BLASTN and BLASTP, using the following default parameters: Genetic code=standard; filter=none; strand=both; cutoff-60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

The amplified DNA is sequenced and analyzed using methods known to those of skill in the art. Determination of the sequence of a nucleic acid sequence of interest can be performed using a variety of sequencing methods known in the art including, but not limited to, sequencing by hybridization (SBH), sequencing by ligation (SBL) (Shendure et al. (2005) *Science* 309:1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., using platforms such as Roche 454, Illumina Solexa, AB-SOLiD, Helicos, Polonator platforms and the like, can also be utilized. A variety of light-based sequencing technologies are known in the art (Landegren et al. (1998) *Genome Res.* 8:769-76; Kwok (2000) *Pharmacogenomics* 1:95-100; and Shi (2001) *Clin. Chem.* 47:164-172).

The amplified DNA can be sequenced by any suitable method. In particular, the amplified DNA can be sequenced using a high-throughput screening method, such as Applied Biosystems' SOLiD sequencing technology, or Illumina's Genome Analyzer. In one aspect of the invention, the amplified DNA can be shotgun sequenced. The number of reads can be at least 10,000, at least 1 million, at least 10 million, at least 100 million, or at least 1000 million. In another aspect, the number of reads can be from 10,000 to 100,000, or alternatively from 100,000 to 1 million, or alternatively from 1 million to 10 million, or alternatively from 10 million to 100 million, or alternatively from 100 million to 1000 million. A "read" is a length of continuous nucleic acid sequence obtained by a sequencing reaction.

"Shotgun sequencing" refers to a method used to sequence very large amount of DNA (such as the entire genome). In this method, the DNA to be sequenced is first shredded into smaller fragments which can be sequenced individually. The sequences of these fragments are then reassembled into their original order based on their overlapping sequences, thus yielding a complete sequence. "Shredding" of the DNA can be done using a number of difference techniques including restriction enzyme digestion or mechanical shearing. Overlapping sequences are typically aligned by a computer suitably programmed. Methods and programs for shotgun sequencing a cDNA library are well known in the art.

The amplification and sequencing methods are useful in the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the genomic DNA in order to determine whether an individual is at risk of developing a disorder and/or disease. Such assays can be used for prognostic or predictive purposes to thereby prophylactically treat an individual prior to the onset of the disorder and/or disease. Accordingly, in certain exemplary embodiments, methods of diagnosing and/or prognosing one or more diseases and/or disorders using one or more of expression profiling methods described herein are provided.

According to an additional aspect, methods are provided for identifying the haploid structure of homologous chromosomes. Haplotype information is useful in describing and interpreting genomes and genetic diversity. Personal haplotypes are useful for personalized medicine. Complete haplotyping information of individuals can also increase the power of genome-wide association studies (GWAS) in discovering genes associated with complex traits. According to this aspect, genetic material from, for example, a single cell from an individual, or two or more cells of the same cell type from an individual, is separated into multiple portions or reaction mixtures such that DNA from homologous chromosomes from the same individual is separated into separate portions. According to one aspect, as a result of the separation of the genomic DNA into multiple portions, the DNA from homologous chromosomes are statistically likely to be separated into separate portions and according to aspects described herein, are separated into separate portions as a result of the separation method described herein. Using amplification, sequencing and analysis methods described herein, or amplification, sequencing and analysis methods known to those of skill in the art, each amplified portion is compared to a reference genome, such as a reference human genome such as described in International Human Genome Sequencing Consortium, *Nature* 431, 931-945 (2004) herein incorporated by reference in its entirety for all purposes and analyzed for single nucleotide polymorphisms (SNPs) associated with each portion. It is to be understood that the method may be applied to other genomes and that reference genomes are readily available to those of skill in the art. SNP analysis has been used to identify haplotypes, such as is described in H. C. Fan et al., *Nat. Biotech.* 29, 51-57 (2011) hereby incorporated by reference in its entirety for all purposes. Based on the sequence information and SNPs, the haplotype of single cells is constructed, such as for example, with a greater than 100 kb haplotype block size. According to an additional aspect, the haplotype of several or multiple single cells from the same individual is compared to determine the complete haplotype of the individual.

According to this aspect, a method of determining the haplotype of a single cell includes the steps of extracting DNA material from tissues, a collection of cells, and/or single cells without significant loss and degradation of DNA molecules. The extracted DNA is then separated into multiple portions or reaction mixtures, with each portion containing a collection of DNA molecules that cover only a subset of the genome. According to this aspect, the separation results in DNA from homologous chromosomes being in separate portions. Each portion or reaction mixture is amplified to produce amplified DNA. The amplified DNA in each portion is sequenced and genotyped. The haplotype of the cell is analyzed by analyzing the sequenced and genotyped DNA. According to one aspect, SNPs are identified in the amplified DNA in each portion which are used to identify DNA from homologous chromosomes. According to an additional aspect, the genomic DNA from a single cell is haplotyped by comparing haplotypes from the amplified DNA in each of the portions.

According to a still additional aspect, de-novo genome assembly methods are provided when a reference genome is not available from a species or when the sample has a complex structural variation as with some cancers. De-novo genome assembly is accomplished by assembling about 100 kb blocks from each sub-genome portion (i.e., a portion of the genomic DNA extracted from a cell or the total genomic DNA) and then mapping blocks with one another. Methods of de-novo genome assembly are known and those principles may be applied to the present method of extracting DNA from a single cell or multiple cells, for example of the same cell type, separating the extracted DNA into multiple portions, amplifying the multiple portions, sequencing the amplified DNA and comparing and analyzing the sequenced DNA to assembly the genome de novo, i.e. without a reference genome.

As used herein, the term "biological sample" is intended to include, but is not limited to, tissues, cells, biological fluids and isolates thereof; isolated from a subject, as well as tissues, cells and fluids present within a subject.

In certain exemplary embodiments, electronic apparatus readable media comprising one or more genomic DNA sequences described herein is provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon one or more expression profiles described herein.

As used herein, the term "electronic apparatus" is intended to include any suitable computing or processing apparatus or other device configured or adapted for storing data or information. Examples of electronic apparatuses suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising one or more expression profiles described herein.

A variety of software programs and formats can be used to store the genomic DNA information of the present invention on the electronic apparatus readable medium. For example, the nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon one or more expression profiles described herein.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

EXAMPLE I

Single Cell DNA Amplification

Cell Selection by Laser Dissection Microscopy

A cell is selected, cut from a culture dish, and dispensed in a tube using a laser dissection microscope (LMD-6500, Leica) as follows. The cells are plated onto a membrane-coated culture dish and observed using bright field microscopy with a 10× objective (Leica). A UV laser is then used to cut the membrane around an individually selected cell such that it falls into the cap of a PCR tube. The tube is briefly centrifuged to bring the cell down to the bottom of the tube. 5 µl lysis buffer (30 mM Tris-Cl PH 7.8, 2 mM EDTA, 20 mM KCl, 0.2% Triton X-100, 12.5 µg/ml Qiagen Protease) is added to the side of the PCR tube and span down. The captured cell is then thermally lysed using the using following temperature schedule on PCR machine: 50° C. 3 hours, 75° C. 20 minutes, 80° C. 5 minutes.

Linear Pre-Amplification

In the linear pre-amplification, a pair of quasi-degenerated primers is used to initiate overlapped amplicons throughout the genomic DNA. The primers are denoted below as NG and NT primers:

```
                                              (SEQ ID NO: 1)
NG 5'-GT GAG TGA TGG TTG AGG TAG TGT GGA
GNNNNNGGG-3'

(SEQ ID NO: 2)
NT 5'-GT GAG TGA TGG TTG AGG TAG TGT GGA
GNNNNNTTT-3'
```

The following buffer is included into the PCR tube and is used for the first amplification: 1.5 µl ThermoPol Buffer (NEB), 1.5 µl Φ29 Reaction Buffer (NEB), 1.0 µl dNTP (10 mM), 26 µl H$_2$O (Ambion) and 0.1 µl NG & NT primer (50 µM).

After the PCR buffer is added into a PCR tube containing the lysed single cell, the sample is heated at 94° C. for 3 minutes to denature the DNA into single stranded DNA. The sample is quenched immediately into ice and is brought to a temperature of about 0° C. during which primer annealing takes place. 0.6 µA of a mixture of polymerases Bst large fragment and Φ29 from New England Biolabs is then added into the PCR tube. The following temperatures and times (thermocycle) are run on the PCR machine.

10° C.—45 seconds
20° C.—45 seconds
30° C.—60 seconds
40° C.—45 seconds
50° C.—45 seconds
62° C.—3 minutes
95° C.—20 seconds The PCR tube is then transferred to ice to quench the reaction and initiate new priming.

In a second and subsequent cycles, a fresh mixture of the polymerases is added to the PCR tube and the following cycles are run on the PCR machine to produce amplicons.

10° C.—45 seconds
20° C.—45 seconds
30° C.—60 seconds
40° C.—45 seconds
50° C.—45 seconds
62° C.—3 minutes
95° C.—20 seconds
58° C.—at least 20 seconds

EXAMPLE II

Further Amplification of Amplicons of Example I Using Standard Methods

Standard PCR amplification is used to exponentially amplify the amplicons produced in Example I as follows. The following reaction buffer is prepared and added to the PCR tube which is being maintained on ice.

3.0 µl ThermoPol Buffer (NEB)
1.0 µl dNTP (10 mM)
26 µl H$_2$O (Ambion)
0.1 µl primer (100 µM) (5'-GT GAG TGA TGG TTG AGG TAG TGT GGA G-3') (SEQ ID NO:3)
1.0 µl DeepVentR (exo-) (New England Biolabs)

Amplification is performed with standard PCR procedures as follows to generate 1-2 µg of DNA material.

94° C.—20 seconds
59° C.—20 seconds
72° C.—3 minutes
Repeat the above cycles 17×
72° C.—5 minutes
4° C.∞

After exponential amplification, DNA can be purified using a Qiagen column and stored for a next procedure to remove the primer end of the DNA amplicons.

Additional methods of amplification known to those of skill in the art can be used as follows.

One of the best known amplification methods is PCR, which is described in detail in U.S. Pat. Nos. 4,683,195, 4,683,202 and 4,800,159, each incorporated herein by reference and discussed herein. While PCR is considered to be an acceptable means of carrying out DNA amplification, it is specifically contemplated that the methods of the present disclosure may be carried out using alternate amplification techniques which would be well known to one of ordinary skill in the art and are briefly discussed below. In PCR, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred. The primers are used in any one of a number of template dependent processes to amplify the target-gene sequences present in a given template sample.

The nucleic acid target for the disclosed DNA amplification method is generally considered to be any nucleic acid or nucleic acid analog capable of being amplified by techniques well known in the art. By way of example, target nucleic acids specifically contemplated in the context of the disclosure, may include, but is not limited to: genomic DNA, cDNA, RNA, mRNA, cosmid DNA, BAC DNA, PAC DNA, YAC DNA, and synthetic DNA. In a contemplated embodiment, genomic DNA is from a prokaryotic or eukaryotic cell or tissue and utilized as the sample DNA in the disclosed DNA amplification method. In other embodiments, poly-A mRNA is isolated and reverse transcribed (referred to as RT) to obtain cDNA, which is then used as the sample DNA for DNA amplification using the presently disclosed method. In other contemplated embodiments, cDNA may be obtained and used as the sample DNA to be amplified. In still another embodiment, RNA or mRNA is directly amplified using the disclosed DNA amplification method, wherein the starting material is an RNA sample rather than a DNA sample.

In PCR, two primer sequences are prepared which are complementary to regions on opposite complementary strands of the target-gene(s) sequence. The primers will hybridize to form a DNA:primer hybrid if the target-gene(s) sequence is present in a sample. An excess of deoxyribonucleoside triphosphates are added to a reaction mixture along with a DNA polymerase, e.g., Taq polymerase, that facilitates template-dependent nucleic acid synthesis.

If the DNA:primer hybrid is formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles," are conducted until a sufficient amount of amplification product is produced.

Next, the amplification product is detected. In certain applications, the detection may be performed by visual means. Alternatively, the detection may involve indirect identification of the product via fluorescent labels, chemiluminescence, radioactive scintigraphy of incorporated radiolabel or incorporation of labeled nucleotides, mass labels or even via a system using electrical or thermal impulse signals.

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Qbeta Replicase, described in PCT Patent Application No. PCT/US87/00880, also may be used as still another amplification method in the present disclosure. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[.alpha.-thio]-triphosphates in one stand of a restriction site also may be useful in the DNA amplification. Such an amplification method is described by Walker et al. (Nucleic Acids Res 20(7):1691-6, 1992), incorporated herein by reference.

Strand Displacement Amplification (SDA) is another method of carrying out isothermal amplification of nucleic acids which involves multiple rounds of strand displacement and synthesis, i.e., nick translation. The SDA technique is described in U.S. Pat. Nos. 5,712,124, 5,648,211 and 5,455,166, herein incorporated by reference. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products are released after digestion. The original template is annealed to another cycling probe and the reaction is repeated.

Other nucleic acid amplification procedures specifically contemplated in the context of the present disclosure include transcription-based amplification systems (rAS), including nucleic acid sequence based amplification (NASBA) and 3SR, Kwoh et al., Proc Natl Acad Sci USA, 86:1173-77, 1989; PCT Patent Application WO 88/10315 et al., 1989 (each incorporated herein by reference). In NASBA, the nucleic acids can be prepared for amplification by standard phenol/chloroform extraction, heat denaturation of a clinical sample, treatment with lysis buffer, and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate target specific sequences.

Other amplification methods, as described in British Patent Application No. GB 2,202,328, and in PCT Patent Application No. PCT/US89/01025, each incorporated herein by reference, may be used in accordance with the present disclosure. In the former application, "modified" primers are used in a PCR-like template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present disclosure. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' of its homology to the template. This primer is then extended by DNA polymerase (exemplified by the large "Klenow" fragment of E. coli DNA polymerase I), resulting in a double-stranded DNA molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without adding enzymes at each cycle. Because of the cyclical nature of this process, the starting nucleic acid sequence can be either DNA or RNA.

Miller et al., PCT Patent Application WO 89/06700 (incorporated herein by reference), disclose a nucleic acid sequence amplification scheme based on the hybridization of a promoter/primer sequence to a target single-stranded DNA followed by transcription of many RNA copies of the sequence. This scheme is not cyclic, i.e., new templates are not produced from the resultant RNA transcripts.

Other suitable amplification methods include "race and "one-sided PCR.". (Frohman, In: PCR Protocols: A Guide To Methods And Applications, Academic Press, N.Y., 1990, each herein incorporated by reference). Methods based on ligation of two (or more) oligonucleotides in the presence of nucleic acid having the sequence of the resulting "di-oligonucleotide," thereby amplifying the di-oligonucleotide, also may be used to amplify DNA in accordance with the present disclosure (Wu et al., Genomics 4:560-569, 1989, incorporated herein by reference).

EXAMPLE III

Removing Priming Sequences from PCR Amplicons

A phosphorothioate nucleotide strategy is used to remove the priming sequences of the amplicon product. The DNA amplicons are re-amplified using dA, dT, dC and phosphorothioated dG. Since the primer sequence does not include the dC nucleotide, the complementary sequence will not contain the dG nucleotide. The product is digested from the 3' end using exonuclease III. However as the phosphorothioate bond cannot be cleaved by exonuclease III, the 3' end can be digested up to the phosphorothioated dG. In the same enzyme mix, Mung Bean exonuclease is also added, which will remove the protruding 5' end formed from exo III cleavage.

The reaction buffer and conditions are as following: 1× Buffer 1 from New England Biolabs, 5 U ExoIII and 0.5 U Mung Bean exonuclease, both enzymes are available from New England Biolabs. The reaction takes 2 minutes at room temperature and can be stopped by adding 5 μl 0.5M EDTA.

After removing primer sequences from DNA product as indicated in the exemplary flow chart below where the steps can occur in sequence or simultaneously, the product can be used for high throughput sequencing platform. For example, the primer sequences can be removed from the 3' end of the top strand and the 3' end of the bottom strand. The primer sequences can then be removed from the 5' end of the top strand and the 5' end of the bottom strand.

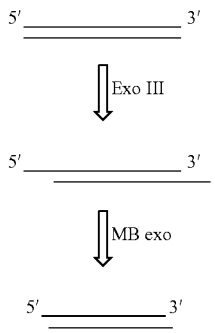

EXAMPLE IV

Removing Priming Sequences from PCR Amplicons

A hemi-methylated primer strategy is used to facilitate removal of the priming sequences of the amplicon product. A hemi-methylated primer is used for the second round of amplification. Then restriction enzyme MspJI or any enzymes with similar properties which requires methyl group for recognizing restriction sites is used. The primer sequence is listed as following:

First Round Amplification Primers:

```
                                        (SEQ ID NO: 1)
GT GAG TGA TGG TTG AGG TCT TGT GGA GNNNNNGGG
```

```
                                        (SEQ ID NO: 2)
GT GAG TGA TGG TTG AGG TCT TGT GGA GNNNNNTTT
```

Second Round Amplification Primers:

```
                                        (SEQ ID NO: 4)
GT GAG TGA TGG TTG AGG TmCT TGT GGA G
```

After the second round of amplification, the enzyme MspJI (0.5 U), buffer 4 (New England Biolabs) and BSA is added into the purified DNA. The reaction is completed in 4 hours at 37° C. The reaction is terminated by column purification.

EXAMPLE V

Useful Labels

Recognition moieties incorporated into primers, incorporated into the amplified product during amplification, or attached to probes are useful in identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure.

Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above.

The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

EXAMPLE VI

Separation Techniques

Following amplification, it may be desirable to separate the amplification products of several different lengths from each other, from the template, and from excess primers for the purpose of analysis or more specifically for determining whether specific amplification has occurred.

In one embodiment, amplification products are separated by agarose, agarose-acrylamide or polyacrylamide gel electrophoresis using standard methods (Sambrook et al., "Molecular Cloning," A Laboratory Manual, 2d Ed., Cold Spring Harbor Laboratory Press, New York, 13.7-13.9: 1989). Gel electrophoresis techniques are well known in the art.

Alternatively, chromatographic techniques may be employed to effect separation. There are many kinds of chromatography which may be used in the present disclosure: adsorption, partition, ion-exchange, and molecular sieve, as well as many specialized techniques for using them including column, paper, thin-layer and gas chromatography (Freifelder, Physical Biochemstry Applications to Biochemistry and Molecular Biology, 2nd ed. Wm. Freeman and Co., New York, N.Y., 1982). Yet another alternative is to capture nucleic acid products labeled with, for example, biotin or antigen with beads bearing avidin or antibody, respectively.

Microfluidic techniques include separation on a platform such as microcapillaries, including by way of example those designed by ACLARA BioSciences Inc., or the LabChip™ by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487, 5,296,375, and 5,856,174 describe apparatus and methods incorporating the various processing and analytical operations involved in nucleic acid analysis and are incorporated herein by reference.

In some embodiments, it may be desirable to provide an additional, or alternative means for analyzing the amplified DNA. In these embodiments, microcapillary arrays are contemplated to be used for the analysis. Microcapillary array electrophoresis generally involves the use of a thin capillary or channel that may or may not be filled with a particular separation medium. Electrophoresis of a sample through the capillary provides a size based separation profile for the sample. Microcapillary array electrophoresis generally provides a rapid method for size-based sequencing, PCR™ product analysis, and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobson et al., Anal Chem, 66:1107-1113, 1994; Effenhauser et al., Anal Chem, 66:2949-2953, 1994; Harrison et al., Science, 261:895-897, 1993; Effenhauser et al., Anal Chem, 65:2637-2642, 1993; Manz et al., J. Chromatogr 593:253-258, 1992; and U.S. Pat. No. 5,904,824, incorporated herein by reference. Typically, these methods comprise photolithographic etching of micron scale channels on a silica, silicon, or other crystalline substrate or chip, and can be readily adapted for use in the present disclosure.

Tsuda et al. (Anal Chem, 62:2149-2152, 1990) describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined, or molded into planar substrates, are filled with an appropriate separation/sieving matrix. Typically, a variety of sieving matrices known in the art may be used in the microcapillary arrays. Examples of such matrices include, e.g., hydroxyethyl cellulose, polyacrylamide, agarose, and the like. Generally, the specific gel matrix, running buffers, and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea to denature nucleic acids in the sample.

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the art are summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include (Schram, Methods Biochem Anal, 34:203-287, 1990) and (Crain, Mass Spectrometry Reviews, 9:505-554, 1990), here incorporated herein by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., Biomedical Environmental Mass Spectrometry 14:111-116, 1987).

Two ionization/desorption techniques are electrospray/ionspray (ES) and matrix-assisted laser desorption/ionization (MALDI). ES mass spectrometry was introduced by Fenn et al., J. Phys. Chem. 88; 4451-59, 1984; PCT Application No. WO 90/14148 and its applications are summarized in review articles, for example, Smith et al., Anal Chem 62:882-89, 1990, and Ardrey, Electrospray Mass Spectrometry, Spectroscopy Europe, 4:10-18, 1992. As a mass analyzer, a quadrupole is most frequently used. The determination of molecular weights in femtomole amounts of sample is very accurate due to the presence of multiple ion peaks that can be used for the mass calculation.

MALDI mass spectrometry, in contrast, can be particularly attractive when a time-of-flight (TOF) configuration is used as a mass analyzer. The MALDI-TOF mass spectrometry was introduced by (Hillenkamp et al., Biological Mass Spectrometry eds. Burlingame and McCloskey, Elsevier Science Publishers, Amsterdam, pp. 49-60, 1990). Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams et al., Science, 246: 1585-87, 1989). More recently, the use of infrared lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides (Berkenkamp et al., Science, 281:260-2, 1998). Berkenkamp also describes how DNA and RNA samples can be analyzed by limited sample purification using MALDI-TOF IR.

In Japanese Patent No. 59-131909, an instrument is described that detects nucleic acid fragments separated either by electrophoresis, liquid chromatography or high speed gel filtration. Mass spectrometric detection is achieved by incorporating into the nucleic acids atoms that normally do not occur in DNA such as S, Br, I or Ag, Au, Pt, Os, Hg.

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, Ann Phys 2:55-75, 1948. The distance between donor and acceptor dyes at which energy transfer efficiency is 50% is referred to as the Forster distance (Ro). Other mechanisms of fluorescence quenching are also known in the art including, for example, charge transfer and collisional quenching.

Energy transfer and other mechanisms that rely on the interaction of two dyes in close proximity to produce quenching are an attractive means for detecting or identifying nucleotide sequences, as such assays may be conducted in homogeneous formats. Homogeneous assay formats differ from conventional probe hybridization assays that rely on the detection of the fluorescence of a single fluorophore label because heterogeneous assays generally require additional steps to separate hybridized label from free label. Several formats for FET hybridization assays are reviewed in Nonisotopic DNA Probe Techniques (Academic Press, Inc., pgs. 311-352, 1992).

Homogeneous methods employing energy transfer or other mechanisms of fluorescence quenching for detection of nucleic acid amplification have also been described. Higuchi et al. (Biotechnology 10:413-417, 1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee et al. (Nucleic Acids Res 21:3761-3766, 1993), discloses areal-time detection method in which a doubly-labeled detector probe is cleaved in a target amplification-specific manner during PCR™ The detector probe is hybridized downstream of the amplification primer so that the 5'-3' exonuclease activity of Taq polymerase digests the detector probe, separating two fluorescent dyes, which then form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use, but only in the context of a method employing a single fluorescent label that is quenched by hybridization to the target.

Signal primers or detector probes that hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product that may be detected as an indication of target amplification. The secondary amplification products generated from signal primers may be detected by means of a variety of labels and reporter groups, restriction sites in the signal primer that are cleaved to produce fragments of a characteristic size, capture groups, and structural features such as triple helices and recognition sites for double-stranded DNA binding proteins.

Many donor/acceptor dye pairs are known in the art and may be used in the present disclosure. These include but are not limited to: fluorescein isothiocyanate (FITC)/tetramethylrhodamine isothiocyanate (TALIC), FITC/Texas Red™ Molecular Probes, FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer, or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl)aminonaphthalene (EDANS). Any dye pairs that produce fluorescence quenching in the detector nucleic acids are suitable for use in the methods of the disclosure, regardless of the mechanism by which quenching occurs. Terminal and internal labeling methods are both known in the art and may be routinely used to link the donor and acceptor dyes at their respective sites in the detector nucleic acid.

Specifically contemplated in the present disclosure is the use or analysis of amplified products by microarrays and/or chip-based DNA technologies such as those described by (Hacia et al., Nature Genet, 14:441-449, 1996) and (Shoemaker et al., Nature Genetics, 14:450-456, 1996). These techniques involve quantitative methods for analyzing large numbers of genes rapidly and accurately. By tagging genes with oligonucleotides or using fixed probe arrays, chip technology can be employed to segregate target molecules as high density arrays and screen these molecules on the basis of hybridization (Pease et al., Proc Natl Acad Sci USA, 91:5022-5026, 1994; Fodor et al, Nature, 364:555-556, 1993).

Also contemplated is the use of BioStar's OIA technology to quantitate amplified products. OIA uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed.

When a positive sample is applied to the wafer, binding occurs between the ligand and the antibody. When substrate is added to complete the mass enhancement, a corresponding change in color from gold to purple/blue results from the increased thickness in the molecular thin film. The technique is described in U.S. Pat. No. 5,541,057, herein incorporated by reference.

Amplified RNA or DNA may be quantitated using the Real-Time PCR technique (Higuchi et al., Biotechnology 10:413-417, 1992). By determining the concentration of the amplified products that have completed the same number of cycles and are in their linear ranges, it is possible to determine the relative concentrations of the specific target sequence in the original DNA mixture. For example, if the DNA mixtures are cDNAs synthesized from RNAs isolated from different tissues or cells, the relative abundance of the specific mRNA from which the target sequence was derived can be determined for the respective tissues or cells. This direct proportionality between the concentration of the amplification products and the relative mRNA abundance is only true in the linear range of the amplification reaction.

The final concentration of the target DNA in the plateau portion of the curve is determined by the availability of reagents in the reaction mixture and is independent of the original concentration of target DNA. Therefore, the first condition that must be met before the relative abundance of a RNA or DNA species can be determined by Real-Time PCR for a collection of RNA or DNA populations is that the concentrations of the amplified products must be sampled when the reaction products are in the linear portion of their curves. The second condition that must be met for an RT-PCR experiment to successfully determine the relative abundance of a particular mRNA species is that relative concentrations of the amplifiable cDNAs must be normalized to some independent standard. The goal of a Real-Time PCR experiment is to determine the abundance of a particular RNA or DNA species relative to the average abundance of all RNA or DNA species in the sample.

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction. The standard technique is described in U.S. Pat. Nos. 5,736,303 and 6,057,107, herein incorporated by reference.

EXAMPLE VII

Identification Techniques

Amplification products must be visualized in order to confirm amplification of the target-gene(s) sequences. One typical visualization method involves staining of a gel with a flourescent dye, such as ethidium bromide or Vistra Green, and visualization under UV light. Alternatively, if the amplification products are integrally labeled with radio- or fluorometrically-labeled nucleotides, the amplification products can be exposed to x-ray film or visualized under the appropriate stimulating spectra following separation.

In one embodiment, visualization is achieved indirectly, using a nucleic acid probe. Following separation of amplification products, a labeled, nucleic acid probe is brought into contact with the amplified products. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used.

The type of label incorporated in DNA amplification products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the amplification reactions can be labeled with a fluorophore, a chromophore or a radioisotope, or by associated enzymatic reaction. Enzymatic detection involves binding an enzyme to a primer, e.g., via a biotin:avidin interaction, following separation of the amplification products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If amplification products are separated using a mass spectrometer no label is required because nucleic acids are detected directly.

A number of the above separation platforms can be coupled to achieve separations based on two different properties. For example, some of the PCR primers can be coupled with a moiety that allows affinity capture, while some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

EXAMPLE VIII

Kits

The materials and reagents required for the disclosed amplification method may be assembled together in a kit.

The kits of the present disclosure generally will include at least the enzymes and nucleotides necessary to carry out the claimed method along with primer sets. In a preferred embodiment, the kit will also contain directions for amplifying DNA from DNA samples.

The kits of the present disclosure also will generally include one or more preselected primer sets and/or probes that may be either specific or non-specific for genes to be amplified. Preferably, the kits will include, in a suitable container means, one or more nucleic acid probes and/or primer sets and means for detecting nucleic acids. In certain embodiments, such as in kits for use in amplification reactions, the means for detecting the nucleic acids may be a label, such as a fluorophore, a radiolabel, an enzyme tag, etc., that is linked to the nucleic acid primer or the nucleotides themselves. It is envisioned that kits may contain pairs of primer sets for each DNA amplification step of the present disclosure. It is also envisioned that kits may contain precipitation solutions to process DNA samples stored on solid mediums according to the precipitation method of the present disclosure.

Exemplary kits are those suitable for use in amplifying whole genomic DNA. In a preferred kit, an exemplary first primer will be provided that has a generic sequence 5' of the random sequence and a random sequence of nucleotides in the middle and a fixed sequence at its 3' end, which hybridizes substantially evenly or evenly across the genomic DNA. The kit will also preferably include a second primer with a generic sequence that is the same as the generic sequence of the first primer. For example, kits may be used to amplify all genes and chromosomal regions, unknown and/or known from an organisms whole genomic or chromosomal DNA. Also included in the kits may be enzymes suitable for amplifying nucleic acids, including various polymerases (RT, Taq, etc.), deoxynucleotides and buffers to provide the necessary single reaction mixture for amplification.

The kits of the present disclosure, may also contain primers with one or more of a variety of other moieties as described above. In another aspect, the kit includes a plurality of polynucleotides, wherein the polynucleotides comprise nucleic acid sequence that is substantially non-self-complementary and substantially non-complementary to other polynucleotides in the plurality, said plurality dispersed in a suitable container. The kit may further comprise a polymerase, such as a strand displacing polymerase, including, for example, one or more of Φ29 Polymerase, Bst Polymerase, Pyrophage 3173, Vent Polymerase, Deep Vent polymerase, TOPOTaq DNA polymerase, Vent (exo-) polymerase, Deep Vent (exo-) polymerase, 9° Nm Polymerase, Klenow fragment of DNA Polymerase I, MMLV Reverse Transcriptase, AMV reverse transcriptase, HIV reverse transcriptase, a mutant form of T7 phage DNA polymerase that lacks 3'-5' exonuclease activity, or a mixture thereof.

In each case, the kits will preferably have distinct containers for each individual reagent and enzyme, as well as for each probe or primer pair. Each biological agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

EXAMPLE IX

Sequencing of Amplicons

The DNA amplicons with the primer sequences removed are then subjected to high-throughput sequencing using methods known to those of ordinary skill in the art and described herein.

EXAMPLE X

General Method of Whole Genome Haplotyping by Sub-Single Cell Genome Amplification and Sequencing A single cell can be isolated and placed into a PCR tube using a mouth pipettor or other methods known to those of skill in the art such as laser dissection or flow cytometry. The tube may then be centrifuged to bring the cell down to the bottom of the tube.

A 1 ul blood sample is collected from a finger prick and then resuspended in 200 ul red blood cell lysis buffer (0.1% Triton X-100, 10 mM EDTA in PBS). After 5 min at room temperature, most red blood cells are lysed while nuclei of the nucleated cells remained intact. A mouth pipet is used to pick out a single cell from the lysed blood and place it into a tube.

60 ul lysis buffer (30 mM Tris-Cl PH 7.8, 2 mM EDTA, 20 mM KCl, 0.3% Triton X-100, 30 mM DTT, 12.5 m/ml Qiagen Protease, 0.1 uM primer 5'-GT GAG TGA TGG TTG AGG TAG TGT GGA G GGG-3') (SEQ ID NO:1) is added to the tube containing the single cell. Cell lysis is performed using the following temperature schedule on a thermal cycler: 50° C. 3 hours, 70° C. 20 minutes. The lysis buffer components and the mild heating procedure are selected to minimize or even prevent double strand breaks and nicks in DNA molecules. DNA resulting from the lysis step is greater than about 100 kb in size. 0.1 uM primer is added into the lysis buffer. Primer is added to the lysis buffer in an amount greater than the concentration of the genomic DNA so as to coat the tube and any pipet placed into the tube with the primer. This serves to inhibit or prevent the genomic DNA from sticking to the tube or pipet tip when inserted into the tube. For tissue samples, one can simply mince the tissue, or use laser micro-dissection to isolate part of a tissue, before DNA extraction with 60 ul lysis buffer. For a collection of cells, one can spin down the cells before lysis with 60 ul lysis buffer.

The following procedure is used to separate extracted DNA molecules into multiple portions with each portion containing a collection of DNA molecules that comprise a subset of the genome. The extracted DNA from a single cell in 60 ul lysis buffer is separated into N equal portions by various methods. The separation procedure results in two homologue alleles being separated into different portions. The likelihood for any allele not separated from its homologue in a diploid cell is 1/N. In single cell haplotyping, N can be made arbitrarily large to ensure complete homologue separation. If multiple identical cells are collected, the same procedure can be repeated with different cells to ensure separation of homologue alleles in at least some single cells.

According to one aspect, low binding PCR tubes and pipet tips are used to prevent DNA molecules from attaching to the wall of the tubes or the pipet tips, amplification primer is added in the lysis buffer to prevent genome DNA sticking to the surface of the tubes and the pipet tips. After the lysis procedure mentioned above, the extracted DNA is separated into N PCR tubes with equal amount by pipetting. Alternatively, the extracted DNA can be separated into N separate portions using microfluidic apparatuses and techniques known to those of skill in the art. The extracted DNA is mildly agitated in a microfluidic device at 4° C. The microfluidic device is designed to have multiple outlet channels (~30 channels). Solutions from each channels are collected for whole genome amplification. Alternatively, for samples of multiple cells or tissues, the extracted DNA can be diluted to an amount that is much less than the amount of genomic DNA in a single cell, for example, for a human cell about 6 pg.

The DNA in each portion is then amplified according to the methods described herein. Alternatively, the DNA in each portion may be amplified according to methods known to those of skill in the art such as multiple displacement amplification (MDA), or by using commercially available whole genome amplification kits such as PicoPlex (Rubicon Genomics), GenomePlex (Sigma-Aldrich), GenomiPhi (GE Healthcare LifeSciences) and the like.

A method of local haplotype analysis is provided by separately identifying single nucleotide polymorphisms (SNPs) in each sub-single cell genome portion, and a method of whole genome haplotyping by comparing local haplotypes from multiple portions is also provided. The sequences of each sub-single cell genome portion is determined separately. The sequences are then compared and mapped with a human reference genome. SNPs are identified separately for the sequences in each portion. Because each portion only contains a small fraction of single cell genome, the sequencing coverage map shows up as 'blocks', with most of the genome uncovered. Statistically, all sequencing reads from the same block belong to the same DNA strand, so all SNPs called within the same block can be linked and phased into the same haplotype. The length of the block of linked SNPs (haplotype block size) depends on the intact DNA size after DNA extraction. Whole genome or chromosome haplotyping can be achieved by repeating the process above with multiple cells. In this case, the haplotype blocks overlap with one another, and the SNPs along one whole chromosome can be phased with high accuracy. Besides genome sequencing, other high throughput genotyping methods (such as SNP microarrays) can also be used for this purpose.

A method of whole genome de novo assembly by separately assembling the genome from each portion followed by mapping the assembled portions with each other is provided. De novo assembly is necessary when a reference genome is not available for a certain species, or the genome variation within a species is significant (e.g. cancer genome). After amplification, the sequence of each sub-single cell genome portion is determined separately. The sequencing reads of each reaction portion are assembled into multiple 'blocks' by regular de-novo assembly algorithms and programs such as CLC Genomics Workbench (CLC bio), SeqMan NGen (DNASTAR), and the like, with a DNA block sizes of, for example, about 100 kb. The assembled blocks are then compared and mapped with each other to build up an assembled genome. Because the 'block' sizes are similar, for example about 100 kb, the complexity for genome assembly by this method scales about linearly with the genome size, while the complexity of traditional de novo assembly methods scales exponentially with the genome size.

EXAMPLE XI

Single Cell Haplotyping

A single white blood cell from de-identified donor P2 was isolated by mouth pipette and lysed with 10 ul lysis buffer in a thermal cycler: 50° C. 3 hours, 70° C. 20 minutes. 60 ul of lysis buffer (without enzyme) was then added into the reaction, and the 70 ul total solution was mixed and separated into 24 PCR tubes. The DNA in the 24 PCR tubes was separately amplified using the method of Example I where a 2 step modified PCR cycle is performed in each of 24 PCR tubes using Deep VentR (exo-) polymerase with both steps of the PCR cycles. The PCR product was purified and 2 loci representing chromosome 1 and chromosome 2 were tested with quantitative PCR. Table 1 below represents quantitative PCR results for the single white blood cell separated into 24 tubes, for loci representing chromosome 1 and chromosome 2. The number denotes the Ct number in qPCR run and represents positive signal with the correspondent loci. "x" denotes negative signal of the correspondent loci.

TABLE 1

| | tube | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| chr1 | x | x | x | x | x | 18.1 | x | x | x | x | x | x |
| chr2 | x | x | x | x | x | x | x | x | x | x | x | x |

| | tube | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| chr1 | x | x | x | x | x | x | x | x | x | x | x | 20.8 |
| chr2 | 22 | x | x | x | x | x | x | x | 20.2 | x | x | x |

Both loci are positive in two tubes, which shows separation of homologue alleles and success in amplifying all four alleles (two homologue pairs from chr1 and chr2). Lack of amplification of an allele in any particular experiment can be due to DNA transfer loss, amplification randomness, or homologue alleles falling in the same tube, however, the methods of the present disclosure minimize these aspects.

EXAMPLE XII

Haplotyping Using Two Cells

Two white blood cells from de-identified donor P2 were isolated by mouth pipette and lysed with 10 ul lysis buffer in a thermal cycler: 50° C. 3 hours, 70° C. 20 minutes. 60 ul of lysis buffer (without enzyme) was then added into the reaction, and the 70 ul total solution was mixed and separated into 12 PCR tubes. (2) The DNA in the 12 PCR tubes were separately amplified using the method of Example I where a 2 step modified PCR cycle was performed in each of 12 PCR tubes using Deep VentR (exo-) polymerase with both steps of the PCR cycles. The PCR product was purified and 8 loci representing chromosome 1-7, 9 were tested with quantitative PCR. Table 2 below represents quantitative PCR results for 2 white blood cells separated into 12 tubes, for loci representing chr 1-chr7 and chr9. Number denotes the Ct number in qPCR run and represents positive signal with the correspondent loci. "x" denotes negative signal of the correspondent loci.

TABLE 2

| | tubes | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| chr1 | x | x | x | 20.5 | x | 21 | x | x | 20.8 | 20.2 | x | x |
| chr2 | x | x | x | x | x | x | 22.5 | x | 21.7 | 26 | x | 25.2 |
| chr3 | x | x | x | x | x | x | x | x | x | x | x | x |
| chr4 | x | 22.2 | x | x | 23 | x | 24.7 | x | 22.5 | x | x | x |
| chr5 | 23.5 | x | x | 22 | x | x | x | x | x | x | x | x |
| chr6 | 25.4 | 26.4 | x | x | x | x | x | x | 23.1 | x | x | x |
| chr7 | x | x | x | 23.1 | x | x | 23.4 | 25.3 | x | 24.5 | x | x |
| chr9 | 25 | x | x | x | x | 25.5 | 24.8 | x | 22.6 | x | x | x |

For loci chr 1, 2, 4, 7, 9, 4 tubes are positive for amplification, representing equal separation of the 4 homologue alleles (2 cells) into 4 out of 12 tubes. For chr 3, no loci is shown due to incomplete amplification with this loci. For chr 5 and chr 6, fewer than 4 tubes show positive signal. This might be due to incomplete amplification of all alleles, or the homologue alleles falling into the same tube. Increasing tube number can ensure most homologue alleles fall into different tubes.

EXAMPLE XIII

Haplotyping without Isolating Single Cells 1 ul blood from donor P1 was dissolved in 100 ul lysis buffer in a thermal cycler: 50° C. 3 hours, 70° C. 20 minutes. The lysed blood was then diluted 400× and 1000×, and 1 ul from the diluted solution was used for amplification. Because of the dilution, each tube was expected to have the DNA level of about ¼ cell and 1/10 cell. Table 3 below represents quantitative PCR results for amplification of DNA from on average ¼ cells (1-5) and 1/10 cell (6-10), for loci representing chr 1-chr7 and chr9. Number denotes the Ct number in qPCR run and represents positive signal with the correspondent loci.

TABLE 3

| | tubes | | | | | | | | | | | |
|---|---|---|---|---|---|---|---|---|---|---|---|---|
| | 1 | 2 | 3 | 4 | 5 | 6 | 7 | 8 | 9 | 10 | Neg | Neg |
| chr1 | 19.4 | x | x | x | x | x | x | x | x | x | x | x |
| chr2 | 23.1 | x | x | x | x | x | x | x | 24.2 | x | x | x |
| chr3 | x | x | x | x | x | x | x | x | x | x | x | x |
| chr4 | x | 21.8 | x | x | x | 21.8 | x | x | x | x | x | x |
| chr5 | x | x | x | x | x | x | x | x | x | 20.9 | x | x |
| chr6 | x | 26.6 | 25.5 | x | x | x | x | x | x | x | x | x |
| chr7 | x | 22.1 | x | x | x | x | x | 25.3 | x | x | x | x |
| chr9 | x | x | x | x | 23.2 | 26.1 | x | x | x | x | x | x |

The even distribution of loci indicates chromosome entanglement is not a significant factor in allele separation using the dilution methods of the present invention. The separation of alleles for chr 2, 4, 6, 7, and 9 demonstrate that single cell separation is not necessary for haplotyping a single cell.

EXAMPLE XIV

Single Cell Whole Genome Amplification

Multiple annealing and looping based amplification cycles (MALBAC) were performed as follows. The SW480 colorectal adenocarcinoma cell line was obtained from American Type Culture Collection (ATCC, Rockville). SW480 cells were maintained in ATCC-formulated Leibovitz's L-15 Medium supplemented with 10% fetal bovine serum (ATCC), 100 I.U./ml Penicillin and 100 ug/ml Streptomycin (ATCC). The cells were treated with 0.25% Trypsin-EDTA and were briefly cultured and attach to PEN-Membrane slides (Leica). The cells were then fixed with 70% ethanol for 3 minutes and washed with PBS. The cells were stained with 0.5% methylene green for about 20 seconds before being washed twice with ddH$_2$O.

Before laser dissection, UV crosslinking was used to damage DNA contamination in low bind PCR tubes. Single cells were dissected using laser microdissection (Leica LMD7000) into individual PCR tubes. After briefly spinning down the single cells to the bottom of PCR tubes, 5 μl of freshly prepared cell lysis buffer (30 mM Tris-Cl PH 7.8, 2 mM EDTA, 20 mM KCl, 0.2% Triton X-100, 12.5 μg/ml QIAGEN Protease) was added into each tube. The lysis of the single cell was performed by the following temperature steps: 50° C. 3 hours, 75° C. 20 minutes, 80° C. 5 minutes. Isolation of single cells can also be performed with other techniques, such as mouth pipetting and flow cytometry.

For pre-amplification, 30 ul of amplification buffer (20 mM Tris-Cl (pH 8.8), 10 mM (NH4)2SO4, 10 mM KCl, 3 mM MgSO4, 0.1% Triton X-100, 0.32 uM Primer GAT3T (GTG AGT GAT GGT TGA GGT AGT GTG GAG NNN NNG GG (SEQ ID NO:5) in the 5' to 3' direction), 0.25 uM Primer GAT3G (GTG AGT GAT GGT TGA GGT AGT GTG GAG NNN NNT TT (SEQ ID NO:6) in the 5' to 3' direction) was added into PCR tubes each containing a lysed single cell, followed by incubating the tube at 94° C. for 3 mins to melt the double-stranded genome DNA into single stranded form. After that, the single-stranded genomic DNA molecules were immediately quenched on ice to increase the efficiency of primer binding. 2.5 Units of Bst large fragment (NEB), or 2 Units of Bst large fragment supplemented with 0.8 Units of Pyrophage 3173 exo- (Lucigen) were then added into each PCR tube and the following temperature steps were performed: 10° C.—45 s, 20° C.—45 s, 30° C.—45 s, 40° C.—45 s, 50° C.—45 s, 65° C.—2 mins, 94° C.—20 s; The tubes were then quickly quenched on ice.

After quenching on ice, the same polymerase mix was added to provide enzyme for the next round of amplification. The following thermo-cycle was performed before quenching the reactions on ice: 10° C.—45 s, 20° C.—45 s, 30° C.—45 s, 40° C.—45 s, 50° C.—45 s, 65° C.—2 mins, 94° C.—20 s, 58° C.—20 s. The above procedures were repeated 4 times resulting in a mixture of amplicons.

Alternatively, after several rounds of cycles following the above procedures, the resulting product includes full amplicons and semi-amplicons. After melting followed by annealing at 58° C., the two ends of an amplicon hybridize into double strand DNA. The restriction enzyme, which recognizes specific sequence in a primer region (e.g., BseGI), can be used to digest amplicons. As a result, only semi-amplicons are intact. The restriction enzyme is heat activated at 80° C. for 20 minutes. Then additional amplification cycles are performed to generate full amplicons. This method produces linear amplification.

The mixture of amplicons was then further amplified by PCR for purposes of next generation sequencing as follows. 30 ul of the amplification mix (20 mM Tris-Cl (pH 8.8), 10 mM (NH4)2SO4, 10 mM KCl, 4 mM MgSO4, 0.1% Triton X-100, 0.66 uM Primer Bio-GAT (/5Biosg/GTG AGT GAT GGT TGA GGT AGT GTG GAG) (SEQ ID NO:7), 2.4 Units of Deep VentR exo- DNA polymerase (NEB)) was freshly prepared and added into the amplicon mixture. Temperature steps of 94° C.—20 s, 59° C.—20 s, 65° C.—1 min, 72° C.—2 min were repeated 18 times generating about 2-3 ug of double-strand DNA products from a single cell for preparing sequencing libraries for next generation sequencing.

The amplification products were determined to have a size distribution of about 500 bp to about 1500 bp, with the 5' end modified with biotin. Quantitative PCR was performed to check for the amplification uniformity for 16 different loci, each on a different chromosome using karyotyping data (see Rochette et al., *Journal of Molecular Biology* 352, 44 (2005) incorporated herein by reference.) Out of the 16 randomly selected loci, 14 of them were amplified well, which is consistent with the ~92% coverage of the whole genome at 30× sequencing depth of single cells. The data is summarized in Table 4 below showing the Ct numbers of randomly selected 16 loci each on a different chromosome.

TABLE 4

| | qPCR | | | | | | | |
|---|---|---|---|---|---|---|---|---|
| | Chr1 | Chr2 | Chr3 | Chr4 | Chr5 | Chr6 | Chr7 | Chr9 |
| Single Cell | 22.5 | 24.4 | 36.5 | 24.8 | 25.4 | 26.9 | 25.5 | 25.2 |
| Positive Control | 22.2 | 24.5 | 29.6 | 24.4 | 24.4 | 24.4 | 25.5 | 25.1 |

| | qPCR | | | | | | | |
|---|---|---|---|---|---|---|---|---|
| | Chr12 | Chr13 | Chr13 | Chr15 | Chr16 | Chr17 | Chr18 | Chr19 |
| Single Cell | 25.8 | 23.9 | 39.0 | 24.7 | 21.3 | 24.3 | 24.2 | 27.0 |
| Positive Control | 26.4 | 26.3 | 30.0 | 23.8 | 20.0 | 25.8 | 23.7 | 22.5 |

The single cell results are consistent with the positive control containing 500 pg of DNA as starting material. Ct numbers of negative controls are all larger than 30 cycles for the primers used for quantitative PCR as follows.

```
                                                  (SEQ ID NO: 8)
Chr1+:   AGG AAA GGC ATA CTG GAG GGA CAT (SEQ ID NO: 9)
Chr1-:   TTA GGG ATG GCA CCA CAC TCT TGA (SEQ ID NO: 10)
Chr2+:   TCC CAG AGA AGC ATC CTC CAT GTT (SEQ ID NO: 11)
Chr2-:   CAC CAC ACT GCC TCA AAT GTT GCT (SEQ ID NO: 12)
Chr3+:   TCA AGT TGC CAG CTG TGG CTG TAT (SEQ ID NO: 13)
Chr3-:   AGA AGG GCA TTT CCT GTC AGT GGA (SEQ ID NO: 14)
Chr4+:   ATG GGC AAA TCC AGA AGA GTC CAG (SEQ ID NO: 15)
Chr4-:   CCA TTC ACT TCC TTG GAA AGG TAG CC (SEQ ID NO: 16)
Chr5+:   AAT AGC GTG CAG TTC TGG GTA GCA (SEQ ID NO: 17)
Chr5-:   TTC ACA TCC TGG GAG GAA CAG CAT (SEQ ID NO: 18)
Chr6+:   TGA ATG CCA GGG TGA GAC CTT TGA (SEQ ID NO: 19)
Chr6-:   TGT TCA TTA TCC CAC GCC AGG ACT (SEQ ID NO: 20)
Chr7+:   ACC AAA GGA AAG CCA GCC AGT CTA (SEQ ID NO: 21)
Chr7-:   ACT CCA CAG CTC CCA AGC ATA CAA (SEQ ID NO: 22)
Chr9+:   TCC CAG CTC TCT CTC TTG CAT CTT (SEQ ID NO: 23)
Chr9-:   AGT GAA GCT GGT GTATGC AGA GGT (SEQ ID NO: 24)
Chr12+:  AGA GGG CTG CTT TAT GCA GGT G (SEQ ID NO: 25)
Chr12-:  CTA CAT TTG GGT CTT TGC TGC CAT G (SEQ ID NO: 26)
Chr13+:  AGC AGC CCC AGG CAG AT (SEQ ID NO: 27)
Chr13-:  CGG AGA GGA CGG TCA CGT TTA C (SEQ ID NO: 28)
Chr14+:  GTC CAG CAC TAG TGA TCT TGT CC (SEQ ID NO: 29)
Chr14-:  CGT GGG AGT TTT GAA ATG CGA TGT (SEQ ID NO: 30)
Chr15+:  CCT GTC TCT GCT CCT GCG (SEQ ID NO: 31)
Chr15-:  TGC ACA CAT GCA CAG TGG AG (SEQ ID NO: 32)
Chr16+:  CTC CAA GGT TCT GCA GCC TC (SEQ ID NO: 33)
Chr16-:  GGT ATG ACT ACA CAT TCA GGC TGG (SEQ ID NO: 34)
Chr17+:  GTG GTA CAT AGT GCA TGG TCC G
```

```
                                        (SEQ ID NO: 35)
Chr17-:  GGC GAC ATA CCC CAA CTT CAT AAG (SEQ ID NO: 36)
Chr18+:  CGT TCT TAG GAC CAA AGG GCT G (SEQ ID NO: 37)
Chr18-:  CCA GCA TCC ATG TCT CTG CAC (SEQ ID NO: 38)
Chr19+:  GCC CAG AGC GCC TGA (SEQ ID NO: 39)
Chr19-:  CCAG CCC CTG GAC CAC T
```

Figure 5A:
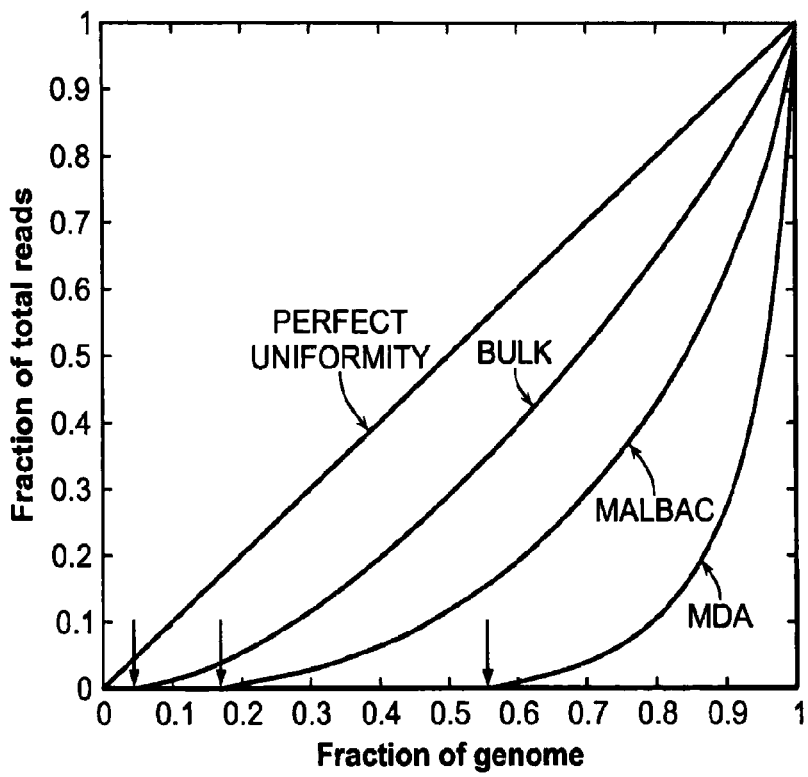
FIG. 5A is a graph of Lorenz curves comparing of coverage uniformity of MALBAC, MDA and bulk sample in terms of the fraction of reads occupied by the fraction of genome. Single cell MALBAC and unamplified bulk results are from the SW480 cancer cell line. The MDA data is from Fan et al., Nature Biotechnology 29, 51 (2011) hereby incorporated by reference herein. Samples have been downsampled when necessary to ~8× depth. (A) Lorenz curves of MALBAC, MDA and bulk sample. Perfectly uniform coverage would result in a diagonal line and larger deviations from the diagonal are indicative of more biased coverage. The arrows indicate the fractions of uncovered genomes by whole genome sequencing (5% for bulk, 15% for MALBAC, 55% for MDA with zero reads).
Figure 5B:
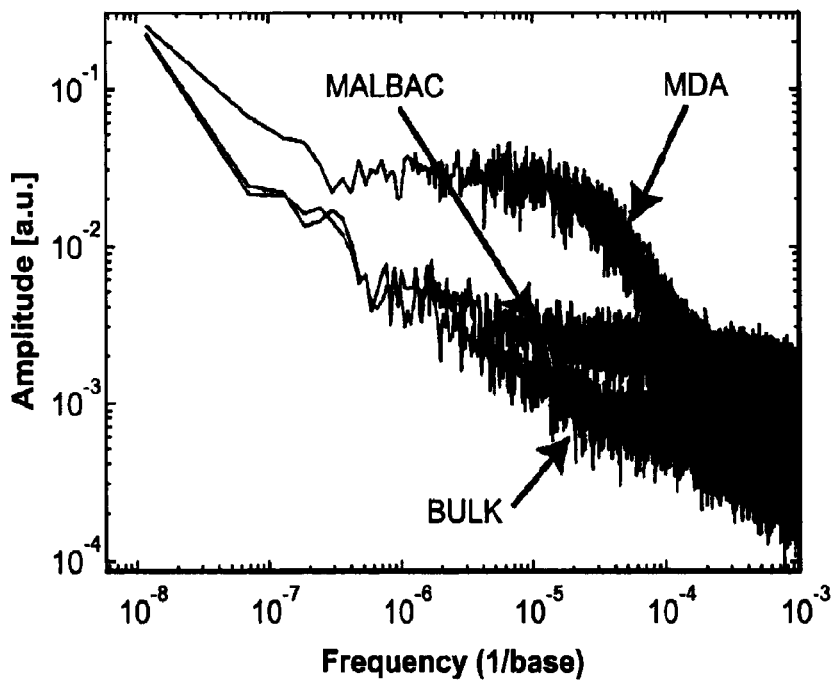
FIG. 5B is a power spectrum of read density throughout the genome (as a function of spatial frequency). MALBAC performs similarly to bulk, while MDA contains large low frequency components, demonstrating that regions of several megabases suffer from under- and over-amplification.

Uniformity of amplifications were analyzed using Lorenz curves depicted in FIG. 5A showing the cumulative fraction of the total reads occupied by a given cumulative fraction of genome comparing bulk, amplification according to the present disclosure (MALBAC) and MDA. Perfectly uniform coverage corresponds to the diagonal line, and large deviations from the diagonal line are indicative of strongly biased coverage. The Lorenz curves in FIG. 5A compare the performance of bulk, MALBAC and MDA, all collected or downsampled when necessary to ~8× sequencing depth. The unamplified bulk sequencing (95% coverage) is the closest to the diagonal. The 85% total coverage of MALBAC at ~8× sequencing depth is similar to the 95% of bulk and better than the 45% of MDA (with the fractions of genome with zero reads being 5%, 15% and 55% respectively, arrows in FIG. 5A).

CNVs are insertions, deletions or multiplications of genome segments, which can vary in size from kilobases to a whole chromosome. They are frequently observed in almost all categories of human tumors. Originating from a single cell, CNVs create genetic variations that are critical to the development and progression of tumors. Single cell CNV analysis with single copy resolution was achieved using the amplification methods described herein. To further investigate the uniformity across the genome, the power spectrum of read density was evaluated in terms of the spatial frequency with units of reciprocal bases. Perfectly even amplification gives a delta function power spectrum. Analysis showed that has a similar power spectrum to that of the unamplified bulk. In contrast, the power spectrum of MDA had considerable amplitudes in the range of tens of kilobases to tens of megabases, resulting in over and under amplification within this range demonstrating that embodiments of the MALBAC method described herein can probe copy number variations (CNV).

With the resolution of single copy afforded by MALBAC's uniform coverage, the CNVs across the whole genomes of two individual cells from SW480 cancer cell line were determined. The two individual cancer cells were different from each other, each exhibiting digitized copy numbers. It was evident this information was otherwise hidden in the average result of the bulk. Hidden Markov model was used to fit the single cell data in order to call CNVs with statistical confidence (SOM). As a control, digital counting results were compared with spectral karyotyping. For example, most chromosomes exist in two copies, as expected from a diploid genome. However, pertinent to the SW480 cancer cell line, chromosome 8 has only one copy and chromosome 17 has three copies. The digital counting and spectral karyotyping results were in good agreement.

To further study CNVs in a cell, the ratio of the two single cells across the entire genome was evaluated. Such normalization removes the fluctuation associated with the residual amplification bias, yielding flat levels across the genome. About 8 abrupt level changes were observed in the entire genome, indicating the eight CNV differences between the two cancer cells. Analysis showed that Cell 1 had three copies, while Cell 2 had two copies in a part of Chromosome 13.

The amplified DNA products were then used for preparing sequencing libraries for SOLiD and Illumina sequencing platforms. After DNA fragmentation and end repairing, the 5' biotin prevented sequencing adapters from being ligated to the amplification primer sequences. By doing this, the percentage of reads that are not mappable to the reference genome due to the amplification primer sequences was reduced.

Single nucleotide variations (SNV) in single cells from the SW480 cell line were analyzed as follows. When a particular SNV first emerges in a single cell, it is not detectable in a cell population by bulk sequencing. This highlights the need for single cell SNV calling. Each individual cell exhibits ~1.6×10$^6$ SNVs (Table 5), as expected from the normal SNV frequency of about one per kilobase.

TABLE 5

|  | Daughter cells | Bulk |
|---|---|---|
| Sequencing depth | 29.2x | 30.3x | 35.5x |
| Percent of genome covered | 92.8 | 92.9 | 98.8 |
| SNVs called | 1,606,073 | 2,400,160 |
| Nascent SNVs missed in Bulk sequencing | 13 | |

The majority of them are consistent with the bulk SNVs, indicating they are common SNVs inherited in early generations of cell lineage. However, amplification errors happen intrinsically at a rate of ~10$^{-5}$, which introduce SNV false positives at a higher frequency than the appearance of nascent SNVs in a single cell. This represents a major challenge for single cell sequencing. To address this issue and to identify unique SNVs in a single cell with no ambiguity, two daughter cells that are divided from the same cell (Table 1) were sequenced. Simultaneous observation of the same SNV indicates its presence in the original single cell because the probability of amplification errors occurring on both daughter cells is negligible, ~10$^{-10}$. Thirteen nascent SNVs were identified, which were otherwise undetectable by bulk sequencing.

Analysis determined that six out of the thirteen nascent SNVs are tightly clustered in a 500 bp region, suggesting their generation was not random throughout the genome. Sequencing data generated by Illumina was mapped using BWA (see *Bioinformatics* 25, 1754 (2009) hereby incorporated by reference. Sequencing data generated by SOLiD was mapped by Bioscope. After mapping, the duplicate reads were removed. The SNVs were called using vcftools with phred-scaled quality score for assertion of variation >50 and allele frequency >=0.5(2). For the pair of daughter cells, 2,459,529 and 2,224,969 SNVs respectively were identified. The SNVs shared by both daughter cells (1,774,887 in total) were then collected. These candidate SNVs were further screened by 10× depth coverage to generate the final list of SNV for this pair of cells. In order to identify nascent SNVs, bulk data was used to screen out SNVs widely existing in population. The SNVs identified in two daughters but not in the bulk were potential candidates of nascent SNVs. However, there were still noticeable amounts of false positives due to systematic error in sequencing or mapping. These false positives were identified and removed by comparing the potential nascent SNV candidates to the SNVs called in an unrelated single cell. After screening out systematic errors, the final list of nascent SNVs was generated by the criterion of having at least 20× coverage depth.

The error rate for the amplification methods described herein was calculated by comparing the SNVs called based on a single cell with those called based on bulk data. The SNVs called in the single cell but not in the bulk are mostly false positives due to the amplification errors. For the pair of daughter cells, we find 51805 and 42705 false positives were determined, which indicates $1.7 \times 10^{-5}$ and $1.4 \times 10^{-5}$ amplification-introduced errors, respectively.

A hidden Markov model was used to determine copy number variations in single cells. Coverage was adjusted for mappability by simulating reads with wgsim and using variable bin sizes such that each bin contained the same number of reads and averaged 250 kb in length. At each bin, the state space was constrained to span from zero copies to 9 copies. A simple transition matrix was chosen that gives a favorable weight to diploid copy numbers but otherwise treats different copy numbers symmetrically. Specifically, the probability of transitioning from a state with copy number m to a state with copy number n is:

$$T(m, n) = \begin{cases} 1 - f/b, & \text{for } m = n = 2 \\ 1 - b/l, & \text{for } m = n \neq 2 \\ (b - f)/l, & \text{for } m \neq n = 2 \\ f/(N - 2)/l, & \text{otherwise} \end{cases}$$

where $f=10^{-9}$ is the frequency with which copy number variations occur, $l=5 \times 10^7$ is the length of a typical CNV, $b=250000$ is the bin size, and $N=10$ is the number of states.

Emission probabilities were inferred from coverage data from a single healthy blood cell using the linear pre-amplification method. It was assumed that this cell did not exhibit copy number variation, and it was denoted by $p_2$ the probability of observing a particular read count in one bin in which the cell is diploid. It was denoted by $p_1$ the corresponding probability for a haploid region. Assuming the observed count from a diploid region is the sum of counts from each haploid independently, then $p_2=p_1 * p_1$, with * denoting convolution. This relationship is readily inverted by taking the square root in Fourier space. Once $p_1$ is obtained, emission probabilities for higher copy states can be determined from the relation $p_n=p_{n-1} * p_1$. To account for sequencing depth, read counts from the cancer cells were scaled to match the overall read depth of the healthy cell when calculating emission probabilities. The most likely state sequence was then determined by the Viterbi algorithm.

Lorenz curves were plotted for bulk, MALBAC and multiple displacement amplification (MDA) respectively. The reads were counted in each 5 kb window and then used for generating Lorenz curves, so the bias within 5 kb was averaged out. The Lorenz curve with 5 kb bin characterizes the bias larger than 5 kb. The bias of MALBAC was within 5 kb. In contrast, the 5 kb Lorenz curve of MDA showed limited improvement, which indicates MDA has much higher bias with range larger than 5 kb.

The sequencing runs for this example are summarized in Table 6 below. Single sw480 cells have an incomplete genome, which is ~90% of reference. The coverage percentage of single cell sequencing is renormalized by the corresponding percentage. * Bst large fragment polymerase (exo-) and Pyrophage 3173 (exo-) are used for MALBAC amplification, which improves the coverage comparing to using Bst polymerase only. **S: SOLiD sequencing platform, I: Illumina sequencing platform.

TABLE 6

| Sample index | Averaged sequence depth | Genome coverage | Notes** |
| --- | --- | --- | --- |
| Normal cells bulk | 5.3x | 97% | S |
| Normal single cell | 6.0x | 65% | S |
| SW480 Bulk | 35.5x/11.8x | 98.8%/90% | I/S |
| Single cell 1 | 11.3x | 85% | S |
| Single cell 2* | 29.2x/8.2x | 92.8%/88.6% | I/S |
| Single cell 3*, the sibling of 2 | 30.3x/8.2x | 92.9%/88.4% | I/S |
| Single cell 4 | 14.6x | 85% | S |
| Single cell 5* | 31.1x/6.8x | 87.9%/81.0% | I/S |
| S6-S13*† | ~0.6x | ~39% | S |

EXAMPLE XV

Prenatal Diagnosis

According to certain aspects of the present disclosure, methods are provided for non-invasive prenatal diagnosis by amplifying genetic material, such as DNA, from a single fetal cell or group of fetal cells or circulating fetal DNA in maternal blood and then analyzing the genetic material. According to certain aspects the entire genome or significant portions of the genome of the fetus can be obtained and analyzed, for example, for fetal abnormalities, anomalies and disorders.

According to certain additional aspects, methods are provided for preimplantation genetic screening (PGS) and diagnosis (PGD). Over 100,000 in vitro fertilization (IVF) procedures are performed in the US every year, and techniques for screening embryos for implantation are desirable. Currently available PGS methods include biopsy procedures on polar body, blastomere, blastocyst, etc., followed by using genetic screening techniques such as fluorescence in situ hybridization (FISH) and polymerase chain reactions (PCR) for detecting specific chromosome aberrations (trisomy 21, etc.) and specific genetic variations known to cause severe phenotypical consequences. In IVF, embryos are grown to reach the two- to twelve-cell stage before implantation. According to certain aspects, a single cell or a few cells from the embryo are extracted and then the genetic material, such as DNA, is amplified according to the methods described herein whereby the entire genome of the embryo can be obtained and analyzed, for example, for fetal abnormalities, anomalies and disorders.

According to certain aspects, nucleated fetal cells from maternal blood are isolated. Nucleic acids, such as DNA, are extracted from a single nucleated fetal cell or from a plurality of nucleated fetal cells. Extracellular fetal nucleic acids can be obtained from maternal blood. See Lo et al., Nature Reviews Genetics, Vol. 8, pp. 71-77 (2007) and Lo et al., Sci. Transl. Med. 2, 61ra91 (2010) hereby incorporated by reference in their entireties. The nucleic acids are then amplified by the linear pre-amplification methods described herein to provide, for example, the entire genome of the fetus or specific genome loci for analysis. Genetic variations are then identified and associated with congenital disorders or with known phenotypical consequences.

Nucleated fetal cells are obtained as follows. Maternal blood is obtained by conventional venipuncture or finger pricking. About 0.1 ml to 100 ml of maternal blood is obtained. Nucleated fetal cells (including fetal nucleated red blood cells, lymphocytes, trophoblasts, etc.) can be isolated as early as ~8 weeks after gestation. Nucleated fetal cells from maternal circulation can be isolated by multiple different methods, including: fluorescence-activated cell sorting (FACS) by scattering and surface markers, magnetic-activated cell sorting, microdissection, cell size separation methods (e.g. by microfluidic devices), cell density separation methods (e.g. by centrifugation), etc.

Nucleic acids, such as DNA, is extracted from nucleated fetal cells as follows using protease assisted cell lysis. Single cells are lysed by 30 ul lysis buffer (30 mM Tris-Cl pH 7.8, 2 mM EDTA, 20 mM KCl, 0.3% Triton X-100, 30 mM dTT, 12.5 ug/ml Qiagen Protease). See, Bianchi et al., Isolation of fetal DNA from nucleated erythrocytes in maternal blood, *Proc. Natl. Acad. Sci. USA* Vol. 87, pp. 3279-3283, May 1990 and Wachtel et al., *Clin. Genet.* 2001: 59; 74-79 (2001) each hereby incorporated by reference in their entireties. Other methods such as alkaline lysis or freeze-thaw lysis can also be applied for nucleic acid extraction or using other methods described herein or known to those of skill in the art.

The extracted nucleic acids can then be amplified as follows. For pre-amplification, 30 ul of amplification buffer (20 mM Tris-Cl (pH 8.8), 10 mM (NH4)2SO4, 10 mM KCl, 3 mM MgSO4, 0.1% Triton X-100, 0.32 uM Primer GAT3T (GTG AGT GAT GGT TGA GGT AGT GTG GAG NNN NNG GG (SEQ ID NO:5) in the 5' to 3' direction), 0.25 uM Primer GAT3G (GTG AGT GAT GGT TGA GGT AGT GTG GAG NNN NNT TT (SEQ ID NO:6) in the 5' to 3' direction) is added into PCR tubes each containing a lysed single cell, followed by incubating the tube at 94° C. for 3 mins to melt the double-stranded genome DNA into single stranded form. After that, the single-stranded genomic DNA molecules are immediately quenched on ice to increase the efficiency of primer binding. 2.5 Units of Bst large fragment (NEB), or 2 Units of Bst large fragment supplemented with 0.8 Units of Pyrophage 3173 exo- (Lucigen) is then added into each PCR tube and the following temperature steps is performed: 10° C.—45 s, 20° C.—45 s, 30° C.—45 s, 40° C.—45 s, 50° C.—45 s, 65° C.—2 mins, 94° C.—20 s; The tubes are then quickly quenched on ice.

After quenching on ice, the same polymerase mix is added to provide enzyme for the next round of amplification. The following thermo-cycle is performed before quenching the reactions on ice: 10° C.—45 s, 20° C.—45 s, 30° C.—45 s, 40° C.—45 s, 50° C.—45 s, 65° C.—2 mins, 94° C.—20 s, 58° C.—20 s. The above procedures are repeated 4 times resulting in a mixture of amplicons.

The mixture of amplicons is then further amplified by PCR for purposes of next generation sequencing as follows. 30 ul of the amplification mix (20 mM Tris-Cl (pH 8.8), 10 mM (NH4)2SO4, 10 mM KCl, 4 mM MgSO4, 0.1% Triton X-100, 0.66 uM Primer Bio-GAT (/5Biosg/GTG AGT GAT GGT TGA GGT AGT GTG GAG) (SEQ ID NO:7), 2.4 Units of Deep VentR exo- DNA polymerase (NEB)) is freshly prepared and added into the amplicon mixture. Temperature steps of 94° C.—20 s, 59° C.—20 s, 65° C.—1 min, 72° C.—2 min were repeated 18 times generating about 2-3 ug of double-strand DNA products from a single cell for preparing sequencing libraries for next generation sequencing.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumina, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome before imaging or sequencing the probes; as well as using PCR or multiplex PCR to amplify specific region(s) of the whole genome before further sequencing or genotyping these regions.

Genetic variations pertinent to prenatal screening and diagnosis mentioned above have a wide range of scale, including but not limited to single nucleotide variations (SNVs), small insertions and deletions (Indels) with size ranged 1-100 bp, copy number variations (CNVs) of genomic length ranged ~100 bp-100 Mbp, sequence inversions and duplications ranged 1 bp-10 Mbp, loss of heterzygosity (LOH) ranged 10 bp-100 Mbps, as well as whole chromosome level abnormalities such as chromosome translocations, aneuploidy, deletion or duplication of part or the whole chromosome.

Examples of "congenital disorders or known phenotypical consequences" include known disorders associated with the above-mentioned genetic variations, such as beta-thalassaemia caused by 4 bp deletion in codons 41 and 42 of the haemoglobin-beta (HBB) gene, and Down's syndrome caused by duplication of chromosome 21 (Trisomy 21). "Known phenotypical consequences" mentioned above include potential health conditions or physical status that are not recognized as congenital disorders, such as potential risks or disposition to certain diseases such as cancer, gender of the fetus, etc. For particular conditions see Cheung et al., Nature Genetics, Vol. 14, pp. 264-268 (1996) (sickle cell anemia and thalassaemia), Belroud, et al., The Lancet, Vol. 361, pp. 1013-1014 (2003) (spinal muscular atrophy)

According to certain additional aspects, one or more cells are biopsied or otherwise isolated from an IVF embryo. Nucleic acids, such as DNA, are extracted from a single cell or from a plurality of cells obtained from the IVF embryo. The nucleic acids are then amplified by the linear pre-amplification methods described herein to provide, for example, the entire genome of the embryo or specific genome loci for analysis. Genetic variations are then identified and associated with congenital disorders or with known phenotypical consequences.

One or more cells from an IVF embryo can be isolated by embryo puncture by micromanipulator. The biopsy or isolation is of a polar body from the embryo; is of trophectoderm from the embryo; is of blastomeres from the embryo, etc. The biopsy is taken from the embryo at day 0 to day 6 of development after fertilization.

Nucleic acids, such as DNA, is extracted from the embryonic cells as follows using protease assisted cell lysis. Single cells are lysed by 30 ul lysis buffer (30 mM Tris-Cl pH 7.8, 2 mM EDTA, 20 mM KCl, 0.3% Triton X-100, 30 mM dTT, 12.5 ug/ml Qiagen Protease). Other methods such as alkaline lysis or freeze-thaw lysis can also be applied for nucleic acid extraction or using other methods described herein or known to those of skill in the art.

The extracted nucleic acids can then be amplified as follows. For pre-amplification, 30 ul of amplification buffer (20 mM Tris-Cl (pH 8.8), 10 mM (NH4)2SO4, 10 mM KCl, 3 mM MgSO4, 0.1% Triton X-100, 0.32 uM Primer GAT3T (GTG AGT GAT GGT TGA GGT AGT GTG GAG NNN NNG GG (SEQ ID NO:5) in the 5' to 3' direction), 0.25 uM Primer GAT3G (GTG AGT GAT GGT TGA GGT AGT GTG GAG NNN NNT TT (SEQ ID NO:6) in the 5' to 3' direction) is added into PCR tubes each containing a lysed single cell, followed by incubating the tube at 94° C. for 3 mins to melt the double-stranded genome DNA into single stranded form. After that, the single-stranded genomic DNA molecules are immediately quenched on ice to increase the efficiency of primer binding. 2.5 Units of Bst large fragment (NEB), or 2 Units of Bst large fragment supplemented with 0.8 Units of Pyrophage 3173 exo- (Lucigen) is then added into each PCR tube and the following temperature steps is performed: 10° C.—45 s, 20° C.—45 s, 30° C.—45 s, 40° C.—45 s, 50° C.—45 s, 65° C.—2 mins, 94° C.—20 s; The tubes are then quickly quenched on ice.

After quenching on ice, the same polymerase mix is added to provide enzyme for the next round of amplification. The following thermo-cycle is performed before quenching the reactions on ice: 10° C.—45 s, 20° C.—45 s, 30° C.—45 s, 40° C.—45 s, 50° C.—45 s, 65° C.—2 mins, 94° C.—20 s, 58° C.—20 s. The above procedures are repeated 4 times resulting in a mixture of amplicons.

The mixture of amplicons is then further amplified by PCR for purposes of next generation sequencing as follows. 30 ul of the amplification mix (20 mM Tris-Cl (pH 8.8), 10 mM (NH4)2SO4, 10 mM KCl, 4 mM MgSO4, 0.1% Triton X-100, 0.66 uM Primer Bio-GAT (/5Biosg/GTG AGT GAT GGT TGA GGT AGT GTG GAG (SEQ ID NO:7)), 2.4 Units of Deep VentR exo- DNA polymerase (NEB)) is freshly prepared and added into the amplicon mixture. Temperature steps of 94° C.—20 s, 59° C.—20 s, 65° C.—1 min, 72° C.—2 min were repeated 18 times generating about 2-3 ug of double-strand DNA products from a single cell for preparing sequencing libraries for next generation sequencing.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumina, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome before imaging or sequencing the probes; as well as using PCR or multiplex PCR to amplify specific region(s) of the whole genome before further sequencing or genotyping these regions.

Genetic variations pertinent to prenatal screening and diagnosis mentioned above have a wide range of scale, including but not limited to single nucleotide variations (SNVs), small insertions and deletions (Indels) with size ranged 1-100 bp, copy number variations (CNVs) of genomic length ranged ~100 bp-100 Mbp, sequence inversions and duplications ranged 1 bp-10 Mbp, loss of heterozygosity (LOH) ranged 10 bp-100 Mbps, as well as whole chromosome level abnormalities such as chromosome translocations, aneuploidy, deletion or duplication of part or the whole chromosome and other chromosomal disorders and genetic disorders known to those of skill in the art. It is to be understood that the listing of certain disorders herein is not intended to be exhaustive but only exemplary. As the methods described herein are intended to analyze the genome of a single cell, any and all disorders that can be identified by analyzing the genome of a cell are included herein as being exemplary of the present disclosure.

Examples of "congenital disorders or known phenotypical consequences" subject to prenatal diagnosis include known disorders associated with the above-mentioned genetic variations, such as beta-thalassaemia caused by 4 bp deletion in codons 41 and 42 of the haemoglobin-beta (HBB) gene, and chromosomal disorders such as Down's syndrome caused by duplication of chromosome 21 (Trisomy 21). "Known phenotypical consequences" mentioned above include potential health conditions or physical status that are not recognized as congenital disorders, such as potential risks or disposition to certain diseases such as cancer, gender of the fetus, etc. Additional disorders which can be diagnosed for a fetus (prenatal diagnosis) or embryo using the methods described herein include cystic fibrosis, sickle cell disease, tay-sachs disease, fragile X syndrome, spinal muscular atrophy, haemoglobinopathies, alpha-thalassemia, X-linked disorders (disorders determined by genes on the X chromosome), spina bifida, anencephaly, congenital heart defects, obesity, diabetes, cancer, fetal gender, fetal RHD, fetal HLA haplotype, paternally derived mutations, chromosomal aneuploidy,

EXAMPLE XVI

Cancer Diagnosis

According to certain aspects of the present disclosure, methods are provided for performing whole genome genetic analysis on a single cancer cell, a few cancer cells, a plurality of cancer cells or a minimal amount of cancer cell material. The present methods are particularly useful where only small amounts of cancer cells are present, i.e. a rare amount, or are able to be obtained or isolated. Examples of such cancer cells include circulating tumor cells (CTCs) in the blood of an individual. During the process of interaction of tumor cells with blood vessels, as well as, metastasis, cancer cells such as tumor cells will invade into the bloodstream. Current diagnostic methods using circulating tumor cells rely on counting of enriched CTC cells. Due to the rare amount of CTC cells in the blood (as rare as 1 in $10^9$ blood cells) and the heterogeneity of CTCs, the enrichment efficiency varies case by case. Counting of CTCs is less reliable and the method is currently under evaluation in clinical trials. CellSearch is the only FDA approved machine for CTC enrichment and counting. The conventional genetic diagnosis with the requirement of ~1 million cells may not be applied to CTCs.

Circulating tumor cells provide a course of cells derived from primary or metastatic sites allowing detection and analysis of cancer cells providing an early diagnosis. Methods described herein allow analysis of DNA from circulating tumor cells, which are usually few or rare in number, as a method of diagnosing an individual with cancer without invasive techniques such as obtaining a sample of tumor tissue by surgical means. Methods described herein allow analysis of DNA from circulating tumor cells, which are usually few or rare in number, as a method of early diagnosis of cancer in an individual where the cancer may be at a very early stage, but nonetheless at a point where cancer cells enter the bloodstream of the individual. Methods described herein provide reliable whole genome amplification that can uniformly amplify the whole genome of single cells, as well as about 10 to about 100 cells, without introducing significant amplification bias and allelic drop-outs. Since the methods described herein can amplify the whole genome or near whole genome of a single cell, the methods described herein have particular utility with circulating tumor cells which are relatively few in number, but can still provide an important early detection of cancer.

According to one aspect, the MALBAC method described herein using multiple annealing and looping based amplification cycles is capable of whole genome amplification of a single cancer cell, such as a tumor cell such as a circulating tumor cell for further analysis. According to one aspect, circulating tumor cells can be enriched from a patient's bloodstream. Tumor cells can also be obtained from a primary site or metastasis by non-open surgery such as fine-needle aspiration (FNA) to provide a sample for minimum sample mass diagnosis (MSMD). In this manner, the obtaining of one or more tumor cells can be considered non-invasive. While the methods described herein have particular application to situations where only a rare amount of cancer cells are available, one of skill in the art will readily understand that the methods also have application where a large amount of cancer cells are available, but where single cell genetic analysis is desired.

According to one aspect, methods for analyzing DNA from a cancer cell are provided. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

Examples of general categories of cancer include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells; in adults most often found in the testicle or ovary; in fetuses, babies and young children, most often found on the body midline, particularly at the tip of the tailbone), blastic tumors (i.e., a typically malignant tumor which resembles an immature or embryonic tissue) and the like. One of skill in the art will understand that this list is exemplary only and is not exhaustive, as one of skill in the art will readily be able to identify additional cancers based on the disclosure herein.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-, related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous Tcell, Hodgkin, non-Hodgkin, primary central nervous system); macroglobulinemia, Waldenstrom; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenström macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

According to certain aspects, circulating tumor cells from the blood of an individual are isolated. Nucleic acids are extracted from one or more circulating tumor cells. The nucleic acids are then amplified by the amplification methods described herein, such as the multiple annealing and looping based amplification cycles described herein (linear preamplification) with or without subsequent exponential amplification, to provide, for example, the entire genome of the cell or specific genome loci for analysis. The genome is then analyzed for genetic variations that are associate with genomic disorders in cancer.

Circulating tumor cells are obtained as follows. Patient blood is obtained by conventional venipuncture. About 10 ml of blood is obtained. Circulating tumor cells can be isolated by multiple different methods, including: commercial CellSearch system (see *Clin. Cancer Res.* 2004, 10, 6897-6904 and *Clin. Cancer Res.* 2010, 16, 2634-2645 each hereby incorporated by reference in its entirety), size based filtration device (see *Am. J. Pathol.* 2000, 156, 57-63 and *Cancer Res.* 2010, 70, 6420-6428 each hereby incorporated by reference in its entirety), wild-field imaging with fiberoptic array scanning technology (see *Proc. Natl. Acad. Sci. USA* 2004, 101, 10501-10504 hereby incorporated by reference in its entirety), antibody-based surface capture in tailored microfluidic devices (see *Lab Chip* 2010, 10, 837-842, *Nature* 2007, 450, 1235-1239, *Anal. Chem.* 2011, 83, 2301-2309, *Angew. Chem.* 2011, 123, 3140-3144 and *Angew. Chem. Int. Ed.* 2011, 50, 3084-3088 each hereby incorporated by reference in its entirety.)

According to certain additional aspects, one or more cells are obtained by fine needle aspiration to isolate cells from a lump or a tissue mass. Nucleic acids, such as DNA, are extracted from a single cell or from a plurality of cells obtained from the fine needle aspiration. The nucleic acids are then amplified by the linear pre-amplification methods described herein to provide, for example, the entire genome of the embryo or specific genome loci for analysis. Genetic variations are then identified and associated with congenital disorders or with known phenotypical consequences.

Cells are biopsied and isolated using fine needle aspiration as follows. The skin above the area to be biopsied is swabbed with an antiseptic solution and draped with sterile surgical towels. After locating the mass for biopsy, using x-rays or palpation, a special needle of very fine diameter (22 or 25 gauge) is passed into the mass. After the needles are placed into the mass, cells are withdrawn by aspiration with a syringe and transferred to a single tube. Cells are preserved and labeled by markers. Single cancer cells are isolated under fluorescent microscope with mouth pipetting or laser dissection.

Nucleic acids, such as DNA, are extracted from CTC cells or cells obtained by fine needle aspiration as follows using protease assisted cell lysis. Single cells are lysed by 30 ul lysis buffer (30 mM Tris-Cl pH 7.8, 2 mM EDTA, 20 mM KCl, 0.3% Triton X-100, 30 mM dTT, 12.5 ug/ml Qiagen Protease). Other methods such as alkaline lysis or freeze-thaw lysis can also be applied for nucleic acid extraction or using other methods described herein or known to those of skill in the art.

The extracted nucleic acids can then be amplified as follows. For pre-amplification, 30 ul of amplification buffer (20 mM Tris-Cl (pH 8.8), 10 mM (NH4)2SO4, 10 mM KCl, 3 mM MgSO4, 0.1% Triton X-100, 0.32 uM Primer GAT3T (GTG AGT GAT GGT TGA GGT AGT GTG GAG NNN NNG GG (SEQ ID NO:5) in the 5' to 3' direction), 0.25 uM Primer GAT3G (GTG AGT GAT GGT TGA GGT AGT GTG GAG NNN NNT TT (SEQ ID NO:6) in the 5' to 3' direction) is added into PCR tubes each containing a lysed single cell, followed by incubating the tube at 94° C. for 3 mins to melt the double-stranded genome DNA into single stranded form. After that, the single-stranded genomic DNA molecules are immediately quenched on ice to increase the efficiency of primer binding. 2.5 Units of Bst large fragment (NEB), or 2 Units of Bst large fragment supplemented with 0.8 Units of Pyrophage 3173 exo- (Lucigen) is then added into each PCR tube and the following temperature steps is performed: 10° C.—45 s, 20° C.—45 s, 30° C.—45 s, 40° C.—45 s, 50° C.—45 s, 65° C.—2 mins, 94° C.—20 s; The tubes are then quickly quenched on ice.

After quenching on ice, the same polymerase mix is added to provide enzyme for the next round of amplification. The following thermo-cycle is performed before quenching the reactions on ice: 10° C.—45 s, 20° C.—45 s, 30° C.—45 s, 40° C.—45 s, 50° C.—45 s, 65° C.—2 mins, 94° C.—20 s, 58° C.—20 s. The above procedures are repeated 4 times resulting in a mixture of amplicons.

The mixture of amplicons is then further amplified by PCR for purposes of next generation sequencing as follows. 30 ul of the amplification mix (20 mM Tris-Cl (pH 8.8), 10 mM (NH4)2SO4, 10 mM KCl, 4 mM MgSO4, 0.1% Triton X-100, 0.66 uM Primer Bio-GAT (/5Biosg/GTG AGT GAT GGT TGA GGT AGT GTG GAG) SEQ ID NO:7), 2.4 Units of Deep VentR exo- DNA polymerase (NEB)) is freshly prepared and added into the amplicon mixture. Temperature steps of 94° C.—20 s, 59° C.—20 s, 65° C.—1 min, 72° C.—2 min were repeated 18 times generating about 2-3 ug of double-strand DNA products from a single cell for preparing sequencing libraries for next generation sequencing.

The genetic analyses to be performed on the resulting amplified nucleic acids can be either on the scale of the whole genome, on selected but significant portions of the whole genome or on specific genome loci known to cause abnormalities. Examples of whole genome analyses includes whole genome sequencing by next generation sequencing methods (Illumina, SoliD, etc.), hybridization-based whole genome genotyping techniques such as Single Nucleotide Polymorphism (SNP) array, comparative genomic hybridization array, etc. Examples of analyzing significant portions of the whole genome includes targeted resequencing and genotyping on specific genome regions such as exome, specific chromosomes, etc. Examples of analyzing specific genome loci includes hybridizing nucleic acid probes to the resulting whole genome amplification product before imaging or sequencing the probes; as well as using PCR or multiplex PCR to amplify specific region(s) of the whole genome before further sequencing or genotyping these regions.

Genetic variations pertinent to cancer diagnosis mentioned above have a wide range of scale, including but not limited to single nucleotide variations (SNVs), small insertions and deletions (Indels) with size ranging 1-100 bp, copy number variations (CNVs) of genomic length ranging ~100 bp-100 Mbp, sequence inversions and duplications ranging 1 bp-10 Mbp, loss of heterzygosity (LOH) ranging 10 bp-100 Mbps, as well as whole chromosome level abnormalities such as chromosome translocations, aneuploidy, deletion or duplication of part or the whole chromosome.

Examples of existing cancer genome variations are provided in publicly available databases including Cancer Genome Anatomy Project (CGAP) from NIH and Catalogue of Somatic Mutations in Cancer (COSMIC).

---

What is claimed is:

1. A method of amplifying the whole genome of a single cell comprising
   (a) providing genomic DNA from the single cell in single stranded form in a reaction vessel;
   (b) adding primers having a common sequence, a variable sequence and a fixed sequence to the reaction vessel to produce a reaction mixture, wherein the common sequence includes G, T and A but not C,
   (c) subjecting the reaction mixture to a low temperature at which annealing of the primers to the single stranded genomic DNA takes place,
   (d) adding at least one of a DNA polymerase having strand displacement activity or 5' to 3' exonuclease activity to the reaction mixture and subjecting the reaction mixture to a temperature at which DNA amplification takes place to produce single or double stranded DNA,
   (e) subjecting the reaction mixture to a temperature to produce single stranded amplicons,
   (f) optionally subjecting the reaction mixture to a temperature to anneal free primer to the 3' end of amplicons thereby maintaining a linear structure to prevent the formation of chimeras,
   (g) repeating steps (c) to (f) to produce amplicons of the genomic DNA, and
   (h) analyzing the genomic DNA for congenital disorders or known phenotypical consequences including whole chromosome level abnormalities, chromosome translocations, aneuploidy, deletion or duplication of part or the whole chromosome, beta-thalassaemia Down's syndrome cystic fibrosis, sickle cell disease, tay-sachs disease, fragile X syndrome, spinal muscular atrophy, haemoglobinopathies, alpha-thalassemia, X-linked disorders (disorders determined by genes on the X chromosome), spina bifida, anencephaly, congenital heart defects, obesity, diabetes, cancer, fetal gender, fetal RHD, fetal HLA haplotype, paternally derived mutations, or chromosomal aneuploidy.

2. The method of claim 1 wherein the primers have the following sequences: 5'-GT GAG TGA TGG TTG AGG TAG TGT GGA GNNNNNGGG-3' (SEQ ID NO:1) and 5'-GT GAG TGA TGG TTG AGG TAG TGT GGA GNNNNNTTT-3' (SEQ ID NO:2).

3. The method of claim 1 wherein the DNA polymerase includes at least one of Φ29 polymerase or Bst polymerase.

4. The method of claim 1 wherein the DNA polymerase includes Φ29 polymerase and Bst polymerase.

5. The method of claim 1 further including the step of removing primer sequences and complementary primer sequences from the 5' end and the 3' end of the amplicons.

6. The method of claim 1 wherein the low temperature at which annealing takes place is between about 0° C. and about 10° C.

7. The method of claim 1 wherein the temperature at which DNA amplification takes place is between about 30° C. and about 65° C.

8. The method of claim 1 wherein the temperature to anneal free primer to the 3' end of amplicons is between about 55° C. and about 60° C.

9. The method of claim 1 wherein the optional step is performed during a second and subsequent thermocycle.

10. The method of claim 1 wherein the single cell is a single fetal cell.

11. The method of claim 1 wherein the single cell is a single fetal cell and the method further comprises
   (h) analyzing the genomic DNA for congenital disorders or known phenotypical consequences including whole chromosome level abnormalities, chromosome translocations, aneuploidy, deletion or duplication of part or the whole chromosome, beta-thalassaemia Down's syndrome cystic fibrosis, sickle cell disease, tay-sachs disease, fragile X syndrome, spinal muscular atrophy, haemoglobinopathies, alpha-thalassemia, X-linked disorders (disorders determined by genes on the X chromosome), spina bifida, anencephaly, congenital heart defects, obesity, diabetes, cancer, fetal gender, fetal RHD, fetal HLA haplotype, paternally derived mutations, or chromosomal aneuploidy.

* * * * *